(12) United States Patent
Kim

(10) Patent No.: US 12,239,467 B2
(45) Date of Patent: Mar. 4, 2025

(54) DISPLAY DEVICE

(71) Applicant: SAMSUNG DISPLAY CO., LTD., Yongin-si (KR)

(72) Inventor: Chul Kim, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 0 days.

(21) Appl. No.: 18/509,469

(22) Filed: Nov. 15, 2023

(65) Prior Publication Data
US 2024/0358330 A1 Oct. 31, 2024

(30) Foreign Application Priority Data

Apr. 27, 2023 (KR) .................. 10-2023-0055266

(51) Int. Cl.
*A61B 5/00* (2006.01)
*A61B 5/024* (2006.01)
*G06F 3/044* (2006.01)
*G09G 3/3233* (2016.01)

(52) U.S. Cl.
CPC ........ *A61B 5/6898* (2013.01); *A61B 5/02433* (2013.01); *G06F 3/044* (2013.01); *G09G 3/3233* (2013.01); *G06F 2203/04105* (2013.01); *G09G 2300/0819* (2013.01); *G09G 2300/0852* (2013.01); *G09G 2354/00* (2013.01); *G09G 2360/14* (2013.01); *G09G 2380/08* (2013.01)

(58) Field of Classification Search
CPC ... A61B 5/6898; A61B 5/02433; G06F 3/044; G06F 2203/04105; G09G 3/3233; G09G 2300/0819; G09G 2300/0852; G09G 2354/00; G09G 2360/14; G09G 2380/08
See application file for complete search history.

(56) References Cited

U.S. PATENT DOCUMENTS 10,398,324 B2    9/2019  Mukkamala et al.
2019/0008399 A1* 1/2019  Mukkamala ......... A61B 5/0261
2024/0000326 A1* 1/2024  Mahajan .............. A61B 5/0077

* cited by examiner

*Primary Examiner* — Abhishek Sarma
(74) *Attorney, Agent, or Firm* — F. Chau & Associates, LLC

(57) ABSTRACT

A display device including: display pixels arranged in a display area of a display panel; light sensing pixels arranged in the display area; a display scan driver configured to drive the display pixels to emit light; a light sensing scan driver configured to drive the light sensing pixels to sense light; and a main driving circuit configured to measure a user's biometric information using light sensing signals received from the light sensing pixels, wherein the main driving circuit displays a preset application program screen during a biometric information measurement period to guide the user's pulse wave signal detection process, and measures the biometric information using pulse wave signals determined to have high accuracy among pulse wave signals detected during the biometric information measurement period.

10 Claims, 24 Drawing Sheets

FIG. 13

| Bio-marker Sensing Results | |
|---|---|
| BP | 130 / 80mmHg |
| HR | 70bpm |
| HRV | 60ms |
| RR | 13bpm |
| BVE | 30 |
| Cardiovascular Health | High |
| Oxygen Saturation | 90% |

DISPLAY DEVICE

CROSS-REFERENCE TO RELATED APPLICATION

This application claims priority under 35 U.S.C. § 119 to Korean Patent Application No. 10-2023-0055266 filed on Apr. 27, 2023 in the Korean Intellectual Property Office, the disclosure of which is incorporated by reference herein in its entirety.

1. TECHNICAL FIELD

The present disclosure relates to a display device capable of measuring biometric information, including but not limited to blood pressure and heart rate.

2. DESCRIPTION OF THE RELATED ART

As society becomes increasingly information-oriented, the demand for display devices continues to rise. Display devices are now integral to various electronic devices including, but not limited to, smartphones, digital cameras, laptops, tablets, navigation systems, and smart televisions. For portable display devices, such as smartphones and tablets, a variety of functions are offered including, but not limited to, image capturing, fingerprint recognition, and face recognition.

Recently, with the increasing focus on the healthcare industry, there have been developments in methods to more easily obtain health-related biometric information. For example, there have been efforts to substitute a traditional blood pressure measuring device that uses an oscillometric method with a portable blood pressure measuring device. However, such portable blood pressure measuring devices need their own separate light source, sensor, and display. This means individuals need to carry the portable blood pressure measuring device separately, in addition to their smartphones or tablets, causing a degree of inconvenience.

Recently, efforts have been made to combine a portable display device like a smartphone and a tablet with a portable blood pressure measurement device. Further, there is a need for methods that allow the measurement of various pieces of biometric information such as heart rate, heart rate variability, respiration, cardiovascular disease, oxygen saturation, and more, using portable display devices in addition to measuring blood pressure.

SUMMARY

Embodiments of the present disclosure provide an image display device capable of detecting a user's bio-signal, such as a photoplethysmography signal or the like. This device can measure various pieces of biometric information such as blood pressure, heart rate, heart rate variability, respiratory rate, oxygen saturation, and the like.

Embodiments of the present disclosure also provide a display device capable of guiding a bio-signal detection process with an image display screen to accurately detect a user's bio-signal, and selectively use the more accurately detected bio-signal to increase the accuracy of measuring biometric information.

According to an embodiment of the present disclosure, there is provided a display device including: display pixels arranged in a display area of a display panel; light sensing pixels arranged in the display area; a display scan driver configured to drive the display pixels to emit light; a light sensing scan driver configured to drive the light sensing pixels to sense light; and a main driving circuit configured to measure a user's biometric information using light sensing signals received from the light sensing pixels, wherein the main driving circuit displays a preset application program screen during a biometric information measurement period to guide the user's pulse wave signal detection process, and measures the biometric information using pulse wave signals determined to have high accuracy among pulse wave signals detected during the biometric information measurement period.

According to an embodiment of the present disclosure, there is provided a display device including: display pixels arranged in a display area of a display panel; light sensing pixels arranged in the display area; infrared light emitting pixels arranged in the display area; a display scan driver configured to drive the display pixels to emit light; a light sensing scan driver configured to drive the light sensing pixels to sense light; a touch sensing unit disposed on a front surface of the display panel to sense a user's touch and output a touch sensing signal, a touch driving circuit configured to generate touch data and touch coordinate data according to a magnitude change and an output position of the touch sensing signal; and a main driving circuit configured to measure the user's biometric information using light sensing signals received from the light sensing pixels, wherein the main driving circuit displays a preset application program screen during a biometric information measurement period to guide the user's pulse wave signal detection process, and measures the biometric information using pulse wave signals determined to have high accuracy among pulse wave signals detected during the biometric information measurement period.

In accordance with a display device according to embodiments of the present disclosure, when light emitted from an image display pixel or a camera flash is reflected from a user's specific body part, the reflected light may be detected by a light sensing pixel of a display panel, and the user's bio-signal such as a pulse wave signal or the like may be detected. Accordingly, the user's various pieces of biometric information such as blood pressure, heart rate, respiratory rate, oxygen saturation, and the like may be detected using various mobile display devices such as a watch type display device, a laptop computer, a pad, and the like.

Further, in accordance with the display device according to embodiments of the present disclosure, the bio-signal detection process may be guided with the image display screen to accurately detect the user's biological signal, and the biometric information may be measured by selectively using the more accurately detected bio-signal. Accordingly, biometric information detection accuracy and reliability may be further improved.

BRIEF DESCRIPTION OF THE DRAWINGS

The above and other features of the present disclosure will become more apparent by describing in detail embodiments thereof with reference to the attached drawings, in which:

FIG. 13 is a diagram showing biometric information measurement results obtained using a mobile display device;

DETAILED DESCRIPTION OF THE EMBODIMENTS

The present disclosure will now be described more fully hereinafter with reference to the accompanying drawings, in which embodiments of the disclosure are shown. This disclosure may, however, be embodied in different forms and should not be construed as limited to the embodiments set forth herein.

It will also be understood that when a layer is referred to as being "on" another layer or substrate, it can be directly on the other layer or substrate, or intervening layers may also be present. The same reference numbers may indicate the same components throughout the specification.

It will be understood that, although the terms "first," "second," etc. may be used herein to describe various elements, these elements should not be limited by these terms. These terms are merely used to distinguish one element from another element. For instance, a first element discussed below could be termed a second element. Similarly, the second element could also be termed the first element.

Each of the features of the various embodiments of the present disclosure may be combined or combined with each other, in part or in whole, and technically various interlocking and driving are possible. Each embodiment may be implemented independently of each other or may be implemented together in an association.

Figure 1:
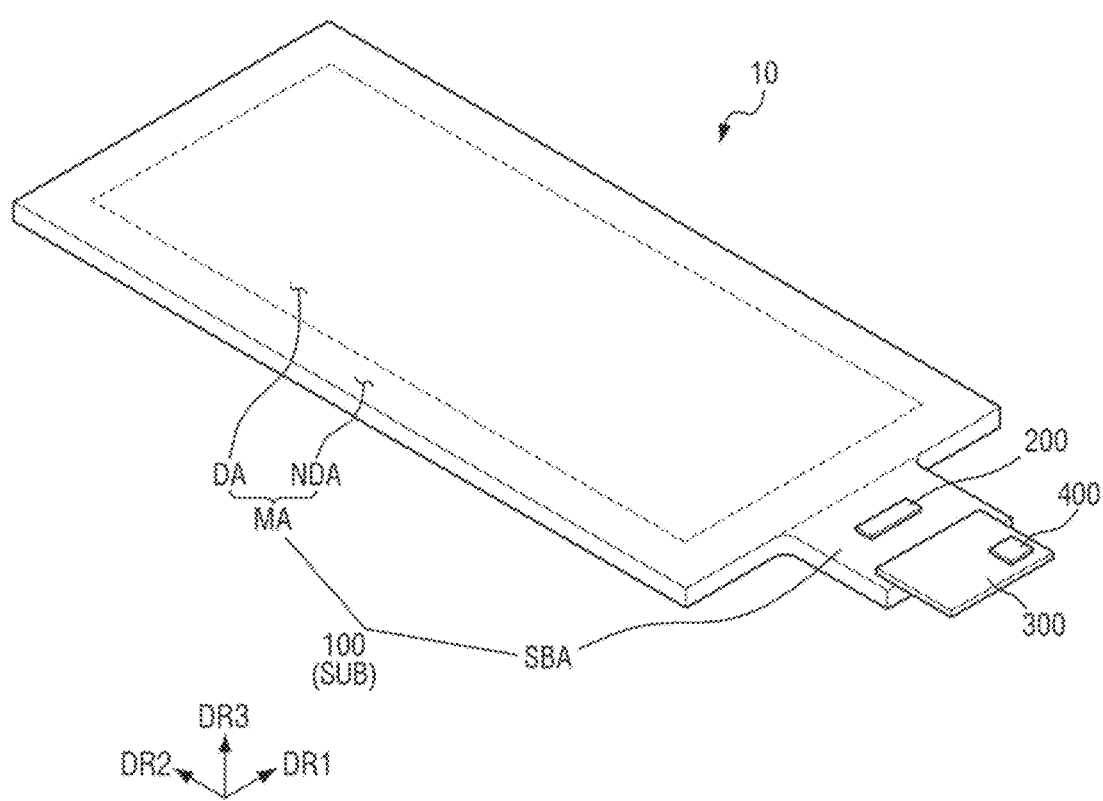
FIG. 1 is a perspective view illustrating a display device according to one embodiment.
Figure 2:
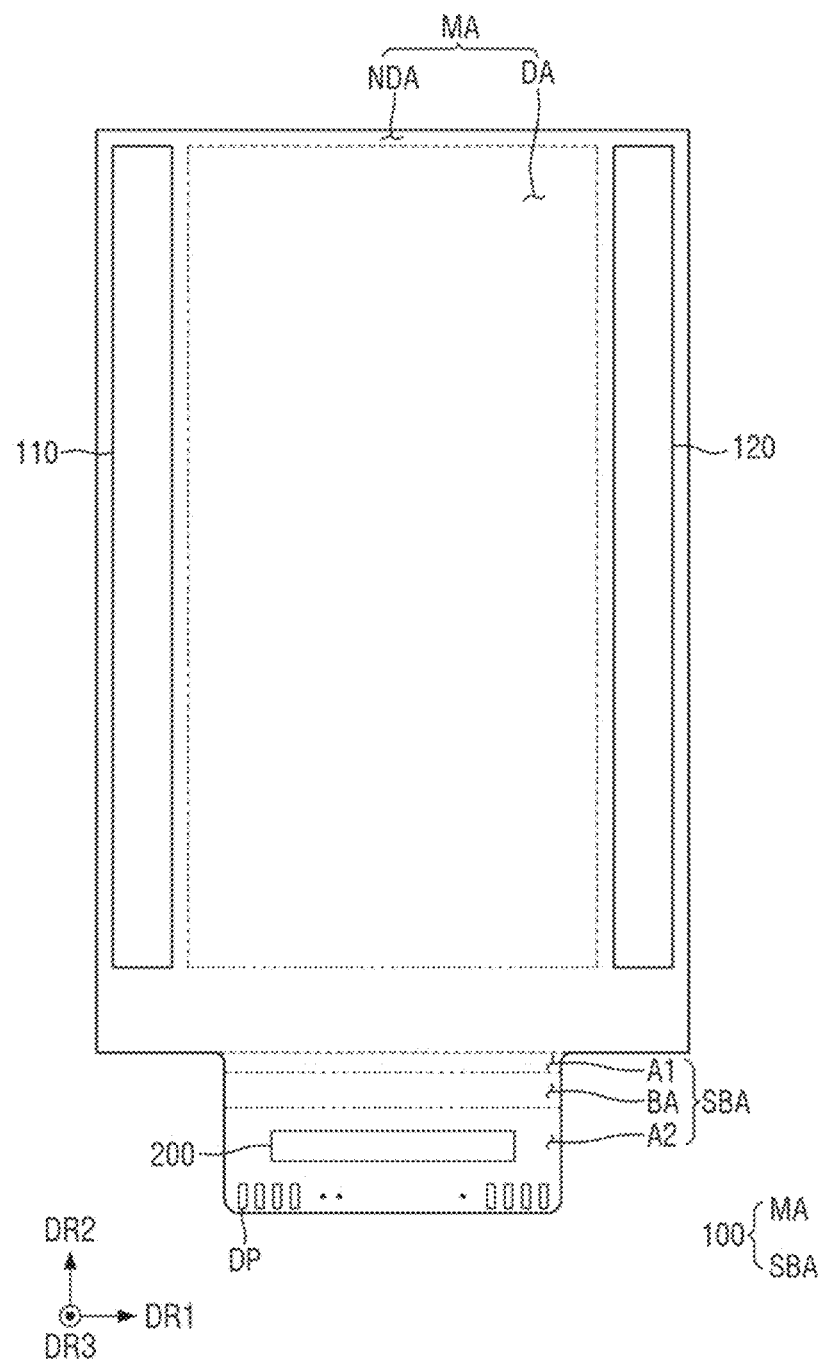
FIG. 2 is a plan view illustrating an arrangement structure of a display panel and a display driving circuit shown in FIG. 1.
Figure 3:
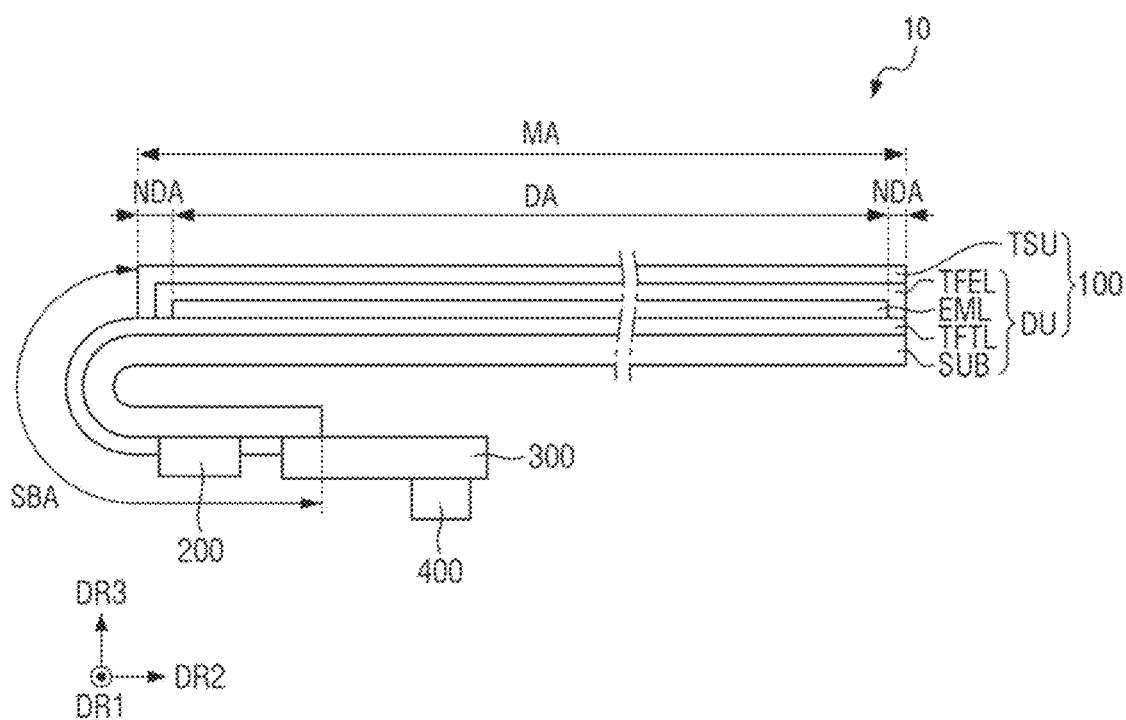
FIG. 3 is a side view showing the configuration of the display device shown in FIG. 1.

FIG. 1 is a perspective view illustrating a display device according to one embodiment. FIG. 2 is a plan view illustrating an arrangement structure of a display panel and a display driving circuit shown in FIG. 1. FIG. 3 is a side view showing the configuration of the display device shown in FIG. 1.

First, referring to FIGS. 1 and 2, a display device 10 according to one embodiment may be applied to portable electronic devices such as a mobile phone, a smartphone, a tablet personal computer (PC), a mobile communication terminal, an electronic organizer, an electronic book, a portable multimedia player (PMP), a navigation system, an ultra mobile PC (UMPC) or the like. Further, the display device 10 according to one embodiment may be applied as a display unit of a television, a laptop, a monitor, a billboard, or an Internet-of-Things (IoT) terminal. Alternatively, the display device 10 according to one embodiment may be applied to wearable devices such as a smart watch, a watch phone, a glasses type display, or a head mounted display (HMD). Further, the display device 10 according to one embodiment may be applied to a dashboard of a vehicle, a center fascia of a vehicle, a center information display (CID)

disposed on a dashboard of a vehicle, a room mirror display in place of side mirrors of a vehicle, or a display disposed on a rear surface of a front seat for rear seat entertainment in a vehicle.

The display device 10 may be a light emitting display device such as an organic light emitting display using an organic light emitting diode, a quantum dot light emitting display including a quantum dot light emitting layer, an inorganic light emitting display including an inorganic semiconductor, and a micro light emitting display using a micro or nano light emitting diode (LED). In the following description, it is assumed that the display device 10 is an organic light emitting display device, but the present disclosure is not limited thereto.

Referring to FIGS. 1 and 3, the display device 10 includes a display panel 100, a main driving circuit 200, a touch sensing unit TSU, a pressure sensing unit PSU (see FIG. 4), a circuit board 300, and a touch driving circuit 400.

The display panel 100 may, in a plan view, be formed in a rectangular shape having short sides in a first direction DR1 and long sides in a second direction DR2 crossing the first direction DR1. A corner where the short side in the first direction DR1 and the long side in the second direction DR2 meet may be right-angled or rounded to have a predetermined curvature. The planar shape of the display panel 100 is not limited to the rectangular shape, and may be formed in another polygonal shape, a circular shape or an elliptical shape. The display panel 100 may be formed to be flat, but is not limited thereto. For example, the display panel 100 may include a curved portion formed at left and right ends and having a constant curvature or a varying curvature. In addition, the display panel 100 may be formed flexibly so that it can be curved, bent, folded, or rolled.

A substrate SUB of the display panel 100 may include a main region MA and a sub-region SBA.

The main region MA may include a display area DA for displaying an image and a non-display area NDA that is a peripheral area of the display area DA.

The non-display area NDA may be disposed adjacent to the display area DA. The non-display area NDA may be an area outside the display area DA. The non-display area NDA may be disposed to surround the display area DA. The non-display area NDA may be an edge area of the display panel 100.

The display area DA includes display pixels for displaying an image, and light sensing pixels for sensing light reflected from a user's body part such as a face or a finger. Further, the display area DA may further include infrared light emitting pixels for emitting infrared light.

The display area DA may occupy most of the main region MA. The display area DA may be disposed at the center of the main region MA.

The display area DA may be divided into an image display area IDA (see FIG. 2) in which only the display pixels are disposed without the light sensing pixels, and a biometric information measurement area FSA in which both the display pixels and the light sensing pixels are disposed. In other words, the light sensing pixels that are used to detect light incident or reflected from the front surface may be disposed together with the display pixels only in a predetermined part of the light sensing area FSA in the display area DA of the display panel 100. An example in which the display pixels and the light sensing pixels are alternately arranged in the display area DA will be described below.

Referring to FIGS. 2 and 3, the sub-region SBA may protrude from one side of the main region MA in the second direction DR2. The length of the sub-region SBA in the second direction DR2 may be less than the length of the main region MA in the second direction DR2. The length of the sub-region SBA in the first direction DR1 may be substantially equal to or less than the length of the main region MA in the first direction DR1.

The sub-region SBA may include a first region A1, a second region A2, and a bending area BA.

The first area A1 is a region protruding from one side of the main region MA in the second direction DR2. One side of the first region A1 may be in contact with the non-display area NDA of the main region MA, and the other side of the first region A1 may be in contact with the bending area BA. In other words, the main region MA may be disposed between the non-display area NDA and the bending area BA.

The second area A2 is an area on which pads DP and the main driving circuit 200 are disposed. The main driving circuit 200 may be attached to driving pads of the second area A2 using a conductive adhesive member such as an anisotropic conductive layer. The circuit board 300 may be attached to the pads DP of the second area A2 using a conductive adhesive member. One side of the second region A2 may be in contact with the bending area BA.

The bending area BA is an area that can be bent. When the bending area BA is bent, the second region A2 may be disposed under the first region A1 and under the main region MA. The bending area BA may be disposed between the first region A1 and the second region A2. One side of the bending area BA may be in contact with the first region A1, and the other side of the bending area BA may be in contact with the second region A2.

As shown in FIG. 3, the sub-region SBA may be bent, and in this case, it may be disposed under the main region MA. The sub-region SBA may overlap the main region MA in a third direction DR3.

The touch sensing unit TSU for sensing a body part such as a finger, an electronic pen, or the like is formed or disposed on the front portion of the display panel 100. The touch sensing unit TSU may include a plurality of touch electrodes to sense a user's touch in a capacitive manner.

The touch sensing unit TSU includes a plurality of touch electrodes arranged to intersect each other in the first and second directions DR1 and DR2. For example, the plurality of touch electrodes include a plurality of driving electrodes arranged to be spaced apart from each other in parallel in the first direction DR1, and a plurality of sensing electrodes arranged to be spaced apart from each other in parallel in the second direction DR2 to intersect the plurality of driving electrodes with an organic material layer or an inorganic material layer interposed therebetween. The plurality of driving electrodes and the plurality of sensing electrodes may be formed to extend to a wiring region between display pixels SP (see FIG. 5) and light sensing pixels LSP (see FIG. 5) arranged in the display area DA so as not to overlap the display pixels SP (see FIG. 5) and the light sensing pixels LSP (see FIG. 5). The plurality of driving electrodes and the plurality of sensing electrodes form a mutual capacitance, and transmit touch sensing signals that vary according to a user's touch to the touch driving circuit 400.

The touch driving circuit 400 supplies touch driving signals to the plurality of driving electrodes and receives the touch sensing signals from the plurality of sensing electrodes. Then, the change in the mutual capacitance between the driving electrodes and the sensing electrodes is sensed according to the change in the magnitude of the touch sensing signal. The touch driving circuit 400 generates touch data according to the change in the mutual capacitance between the driving electrodes and the sensing electrodes and obtains a position where a touch is sensed. Accordingly, coordinate data of the position where the touch is sensed may be supplied to the main driving circuit 200.

Figure 4:
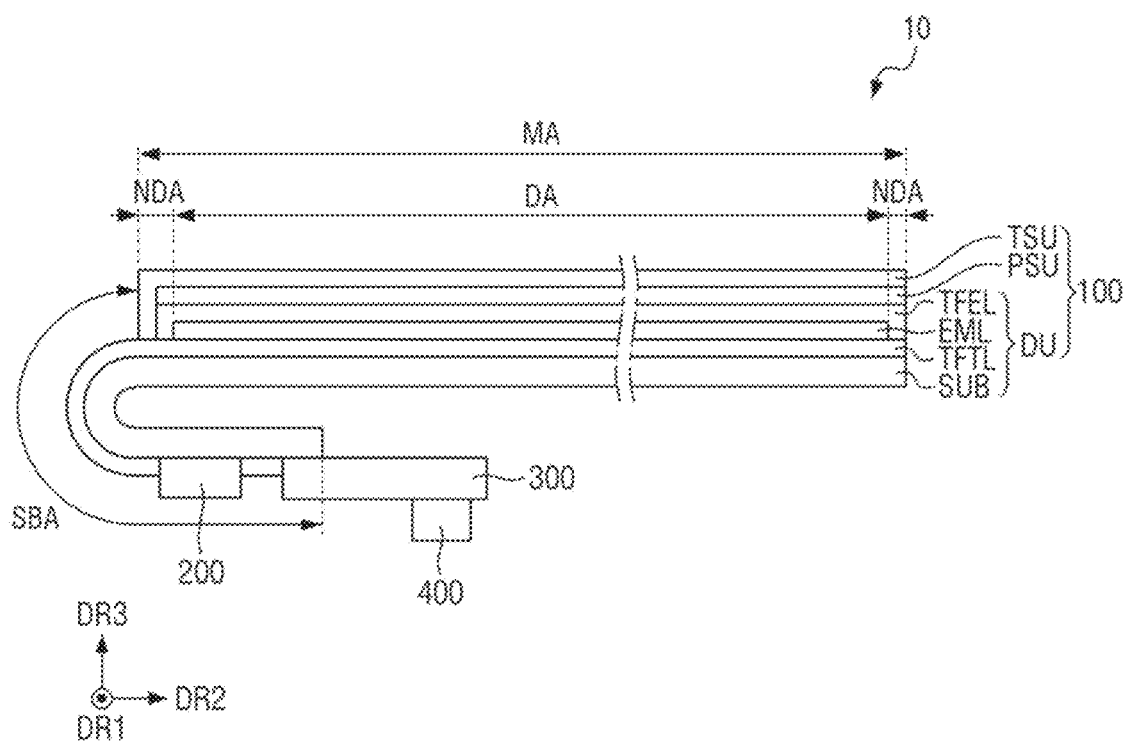
FIG. 4 is a side view of another embodiment illustrating the configuration of the display device shown in FIG. 1.

FIG. 4 is a side view of another embodiment illustrating the configuration of the display device shown in FIG. 1. Like the embodiment of FIG. 3, in FIG. 4 there is provided a display module DU that includes the substrate SUB as well as a thin film transistor layer TFTL, an emission layer EML and an encapsulation layer TFEL.

The pressure sensing unit PSU for sensing the pressure applied by a body part such as a finger or the like may be disposed or formed on the front surface of the display panel 100, for example, on the surface between the display panel 100 and the touch sensing unit TSU. The pressure sensing unit PSU may be formed on the rear surface of the substrate SUB, in another embodiment.

The pressure sensing unit PSU is required in the case of detecting absolute blood pressure-related measurement values, but may not be required in the case of detecting relative blood pressure-related measurement values. Therefore, as shown in FIG. 3, the pressure sensing unit PSU may not be formed.

In the case where the pressure sensing unit PSU is formed, the pressure sensing unit PSU may be formed of a transparent sheet type in which a plurality of transparent electrodes are arranged in vertical and horizontal directions, and may be disposed on the front surface of the main area MA. Alternatively, the pressure sensing unit PSU may be disposed or formed inside or on the front portion of the display panel 100.

The pressure sensing unit PSU includes a plurality of pressure sensing electrodes arranged to intersect each other in the first direction DR1 and the second direction DR2. The plurality of pressure sensing electrodes include a plurality of lower electrodes arranged to be spaced apart from each other in parallel in the first direction DR1, and a plurality of upper electrodes arranged to be spaced apart from each other in parallel in the second direction DR2 to intersect the plurality of lower electrodes with a transparent inorganic (or organic) material layer interposed therebetween. The plurality of lower electrodes and the plurality of upper electrodes form a self-capacitance with a transparent inorganic (or organic) material layer interposed therebetween, and transmit pressure sensing signals that vary according to a user's touch pressure to the touch driving circuit 400.

Figure 5:
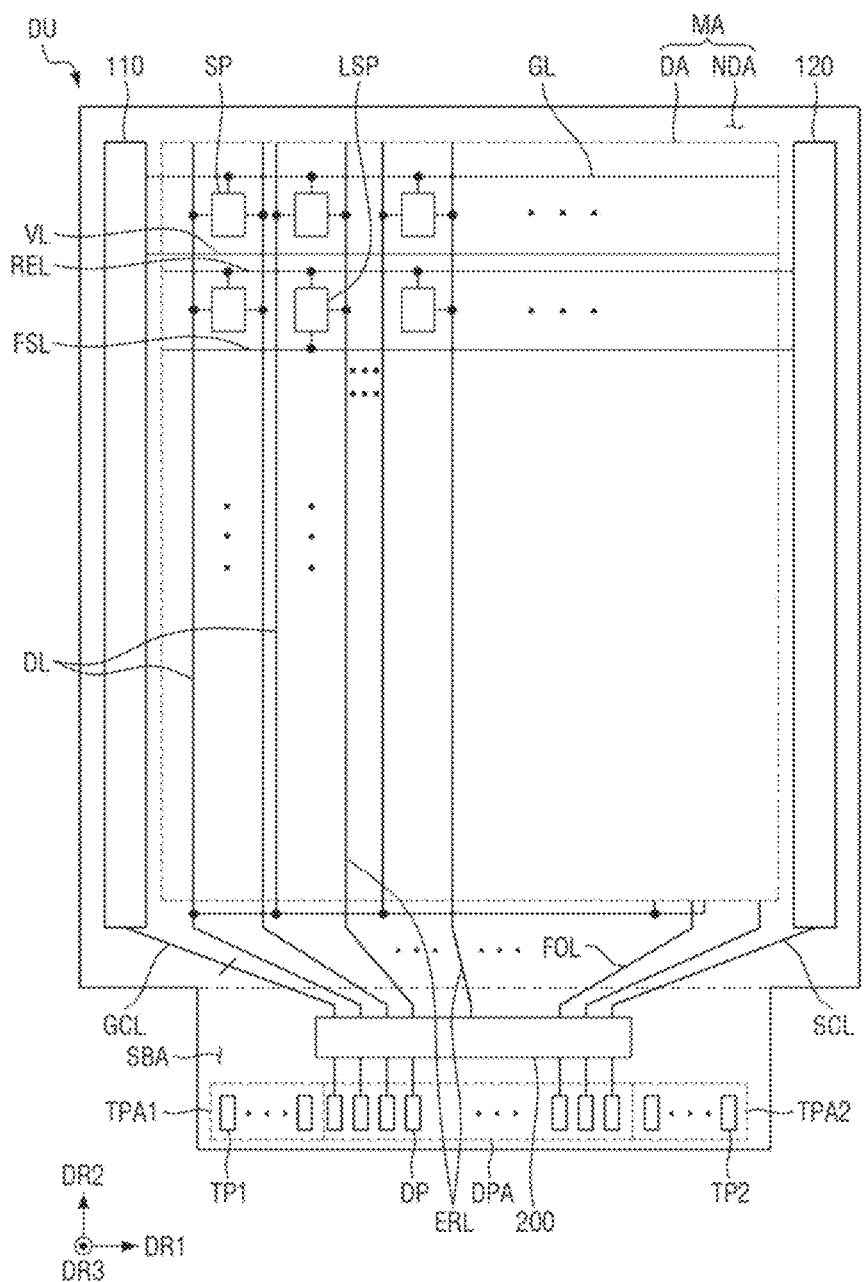
FIG. 5 is a layout diagram schematically showing an example of the display panel illustrated in FIGS. 1 to 4.

When the pressure sensing unit PSU is disposed on the front surface of the display panel 100, the pressure sensing electrodes, e.g., the plurality of lower electrodes and the plurality of upper electrodes, of the pressure sensing unit PSU may be formed to extend to the wiring region between the display pixels and the light sensing pixels arranged in the display area DA so as not to overlap the display pixels SP (see FIG. 5) and the light sensing pixels LSP (see FIG. 5). Additionally, the touch driving circuit 400 may supply a reference voltage to the lower electrodes of the pressure sensing unit PSU, and receive pressure sensing signals from the upper electrodes thereof, thereby sensing the changes in the self-capacitance of the pressed areas using the pressure sensing signals. Accordingly, the touch driving circuit 400 may generate pressure data according to the amount of change in the self-capacitance and sensing coordinate data of a position where a touch is sensed and supply the generated data to the main driving circuit 200. The pressure sensing unit PSU may be applied to various other structures in addition to the structure using the pressure sensing electrodes, and is not limited to the description of FIGS. 3 and 4.

The circuit board 300 may be attached to one end of the sub-region SBA. Thus, the circuit board 300 may be electrically connected to the display panel 100 and the main driving circuit 200. The display panel 100 and the main driving circuit 200 may receive digital video data, timing signals, and driving voltages through the circuit board 300. The circuit board 300 may be a flexible printed circuit board, a printed circuit board, or a flexible film such as a chip on film.

The main driving circuit 200 may generate electrical signals such as data voltages and control signals for driving the display panel 100. The touch driving circuit 400 including the main driving circuit 200 may be formed as an integrated circuit (IC) and attached onto the display panel 100 or the circuit board 300 by a chip on glass (COG) method, a chip on plastic (COP) method, or an ultrasonic bonding method, but the present disclosure is not limited thereto. For example, the touch driving circuit 400 including the main driving circuit 200 may be attached onto the circuit board 300 by a chip on film (COF) method.

FIG. 5 is a layout diagram schematically showing an example of the display panel illustrated in FIGS. 1 to 4. For example, FIG. 5 is a layout diagram illustrating the display area DA and the non-display area NDA of the display module DU before the touch sensing unit TSU is formed thereon.

Referring to FIG. 5 together with FIGS. 3 and 4, a display scan driver 110, a light sensing scan driver 120, and a main driving circuit 200 may be disposed on the display panel 100 of the display device 10 according to one embodiment. Further, a touch driving circuit 400 and a power supply unit may be disposed on the circuit board 300 connected to the display panel 100. Here, the main driving circuit 200 and the touch driving circuit 400 may be integrally formed of a one-chip type, and may be mounted onto the display panel 100 or the circuit board 300. However, hereinafter, for simplicity of functional description, an example in which the main driving circuit 200 and the touch driving circuit 400 are formed as different integrated circuits will be described.

Referring to FIG. 5, the display panel 100 may include the display pixels SP, the light sensing pixels LSP, display scan lines GL, emission control lines VL, data lines DL, sensing scan lines FSL, sensing reset lines REL, and light sensing lines ERL that are disposed in the display area DA. Each of the display scan driver 110 and the light sensing scan driver 120 are disposed in the non-display area NDA.

The display scan lines GL sequentially supply the display scan signals applied in units of horizontal lines from the display scan driver 110 to the display pixels SP and light sensing pixels LSP for each horizontal line. The display scan lines GL may extend in the first direction DR1 and may be spaced apart from each other in the second direction DR2 intersecting the first direction DR1.

The emission control lines VL sequentially supply the emission control signals applied in units of horizontal lines from the display scan driver 110 to the display pixels SP and the light sensing pixels LSP for each horizontal line. The emission control lines VL may extend in the first direction DR1 to be in parallel with the display scan lines GL, and may be spaced apart from each other in the second direction DR2 intersecting the first direction DR1.

The data lines DL may supply the data voltage received from the main driving circuit 200 to the plurality of display pixels SP. The plurality of data lines DL may extend in the second direction DR2 and may be spaced apart from each other in the first direction DR1.

The light sensing scan lines FSL sequentially supply the sensing scan signals applied in units of horizontal lines from the light sensing scan driver 120 to the plurality of light sensing pixels LSP. The light sensing scan line FSL may extend in the first direction DR1 and may be spaced apart from each other in the second direction DR2 intersecting the first direction DR1.

The sensing reset lines REL sequentially supply the sensing reset signals applied in units of horizontal lines from the light sensing scan driver 120 to the plurality of light sensing pixels LSP for each horizontal line. The sensing reset lines REL may extend in the first direction DR1 to be in parallel with the light sensing scan lines FSL, and may be spaced apart from each other in the second direction DR2 intersecting the first direction DR1.

The light sensing lines ERL are connected between the light sensing pixels LSP and the main driving circuit 200 to supply the light sensing signals outputted from the light sensing pixels LSP to the main driving circuit 200. The light sensing lines ERL may be disposed and extended in the second direction DR2 according to the arrangement direction of the main driving circuit 200, and may be spaced apart from each other in the first direction DR1.

The non-display area NDA may surround the display area DA. The non-display area NDA may include the display scan driver 110, the light sensing scan driver 120, fan-out lines FOL, gate control lines GCL, and light sensing control lines SCL.

The display pixels SP and the light sensing pixels LSP may form a first unit pixel and may be arranged in a matrix form in the first direction DR1 and the second direction DR2 in the display area DA. When at least one infrared light emitting pixel is additionally disposed in the display area DA, the display pixels SP and at least one infrared light emitting pixel may form a second unit pixel, and the second unit pixels and the first unit pixels may be alternately arranged in a matrix form in the display area DA.

For example, three display pixels SP that respectively display red, green, and blue light, and one light sensing pixel LSP may form one first unit pixel. In this case, four pixels may form one first unit pixel. In addition, three display pixels SP that respectively display red, green, and blue light, and one infrared light emitting pixel may form one second unit pixel. In this case, four pixels may form one second unit pixel. The first unit pixels and the second unit pixels may be alternately arranged in horizontal or vertical stripes in a matrix form. Alternatively, the first unit pixels and the second unit pixels may be alternately arranged in a zigzag shape in a plan view, and may be arranged in a matrix form in one diagonal direction.

Each of the red, green, and blue display pixels SP and the infrared light emitting pixels may be connected to any one of the display scan lines GL and any one of the emission control lines VL. During an image display period, the red, green, and blue display pixels SP may receive the data voltage of the data line DL according to the display scan signal of the display scan line GL and the emission control signal of the emission control line VL, and may supply a driving current to the light emitting element according to the data voltage, thereby emitting light. Here, during the measurement period of biometric information such as blood pressure, heart rate, oxygen saturation, blood vessel elasticity, and the like, the display pixels SP displaying at least one color among the red, green, and blue display pixels SP may selectively receive the data voltage for light emission together with the display scan signal and the emission control signal and display light. In other words, the display pixels SP, which exhibit at least one color among the red, green, and blue display pixels SP, may selectively receive the data voltage for light emission in conjunction with the display scan signal and the emission control signal, subsequently producing light. Further, during the measurement period of biometric information such as blood pressure, heart rate, and the like, the infrared light emitting pixels may selectively receive the data voltage for light emission together with the display scan signal and the emission control signal, and consequently emit infrared light.

The light sensing pixels LSP may be alternately arranged with the red, green, and blue display pixels SP in a vertical or horizontal direction. Each of the light sensing pixels LSP may be connected to one of the light sensing scan lines FSL, one of the sensing reset lines REL, and one of the light sensing lines ERL. During the measurement period of biometric information such as blood pressure, respiratory rate, oxygen saturation, or the presence or absence of a cardiovascular disease, each of the light sensing pixels LSP is reset in response to the sensing reset signal from the sensing reset lines REL. Subsequently, they may generate the light sensing signal corresponding to the amount of light reflected and incident from the front surface. Further, each of the light sensing pixels LSP may transmit the light sensing signal to the light sensing line ERL in response to the sensing scan signal from the light sensing scan lines FSL.

Alternatively, each of the light sensing pixels LSP may be connected to one of the display scan lines GL in units of horizontal lines. Each of the light sensing pixels LSP may generate the light sensing signal corresponding to the amount of light reflected and incident from the front surface, and may output the light sensing signal to the light sensing line ERL in response to the display scan signal inputted through the display scan line GL.

The display scan driver 110 may be provided in the non-display area NDA. Although the display scan driver 110 is illustrated to be disposed on one side (e.g., left side) of the display panel 100, it is not limited to that shown in the drawings herein. For example, the display scan driver 110 may be disposed on both sides (e.g., left and right sides) of the display panel 100.

The display scan driver 110 may be electrically connected to the main driving circuit 200 through the gate control lines GCL. The display scan driver 110 receives the scan control signal from the main driving circuit 200, and sequentially generates the display scan signals in units of horizontal line driving periods according to the scan control signal and sequentially supplies them to the display scan lines GL. Further, the display scan driver 110 may sequentially generate the emission control signals according to the scan control signal from the main driving circuit 200 and sequentially supply them to the emission control lines VL.

The gate control lines GCL may extend from the main driving circuit 200 to the display scan driver 110 according to the arrangement position of the display scan driver 110. The gate control lines GCL may supply the scan control signals received from the main driving circuit 200 to the display scan driver 110.

The light sensing scan driver 120 may be disposed in another non-display area NDA different from that of the display scan driver 110. FIG. 5 illustrates that the light sensing scan driver 120 is disposed on the other side (for example, the right side) of the display panel 100, but the present disclosure is not limited thereto. The light sensing scan driver 120 may be electrically connected to the main driving circuit 200 through the light sensing control lines SCL. The light sensing scan driver 120 receives the light sensing control signal from the main driving circuit 200, and sequentially generates the reset control signals and the light sensing scan signals in units of horizontal line driving periods according to the light sensing control signal. Then, the sequentially generated reset control signals are sequentially supplied to the sensing reset lines REL. Further, the light sensing scan driver 120 may sequentially generate the sensing scan signals according to the light sensing control signal from the main driving circuit 200 and sequentially supply them to the sensing scan lines FSL.

The light sensing control lines SCL may extend from the main driving circuit 200 to the light sensing scan driver 120 according to the arrangement position of the light sensing scan driver 120. The light sensing control lines SCL may supply the light sensing control signals received from the main driving circuit 200 to the light sensing scan driver 120.

The sub-region SBA may include the main driving circuit 200, a display pad area DPA, and first and second touch pad areas TPA1 and TPA2. The display pad area DPA, the first touch pad area TPA1, and the second touch pad area TPA2 may be disposed at the edge of the sub-region SBA. The display pad area DPA, the first touch pad area TPA1, and the second touch pad area TPA2 may be electrically connected to the circuit board 300 by using an anisotropic conductive layer or a low-resistance high-reliability material such as SAP. The first touch pad area TPA1 may include a plurality of first touch pads TP1 and the second touch pad area TPA2 may include a plurality of second touch pads TP2.

The fan-out lines FOL may extend from the main driving circuit 200 to the display area DA. Further, the fan-out lines FOL are connected such that the data voltage received from the main driving circuit 200 may be supplied to each of the plurality of data lines DL.

The main driving circuit 200 may output signals and voltages for driving the display panel 100 to the fan-out lines FOL. The main driving circuit 200 may supply a data voltage to the data line DL through the fan-out lines FOL. The data voltage may be supplied to the plurality of display pixels SP to determine the luminance of the display pixels SP. The main driving circuit 200 may supply the scan control signal to the display scan driver 110 through the gate control line GCL.

The main driving circuit 200 receives the light sensing signals from the light sensing pixels LSP through the light sensing lines ERL, and detects a photoplethysmography signal corresponding to the change in the magnitudes of the light sensing signals, in other words, pulse wave signals. At this time, the main driving circuit 200 may guide a pulse wave signal detection process with a preset application program screen so that the user's pulse wave signals may be accurately detected, and may analyze the pulse wave signals to sample and select more accurately detected pulse wave signals. In other words, the main driving circuit 200 can guide a pulse wave signal detection process through a preset application program screen, enabling the precise detection of the user's pulse wave signals. It can then analyze the pulse wave signals to sample and select the pulse wave signals that have been detected with greater accuracy. Then, the main driving circuit 200 analyzes the pulse wave signals in units of preset periods to measure biometric information such as blood pressure, heart rate, heart rate variability, respiratory rate, blood vessel elasticity, the occurrence or non-occurrence of cardiovascular disease, or oxygen saturation. Accordingly, the main driving circuit 200 may display the measurement results of the biometric information such as blood pressure, heart rate, heart rate variability, respiratory rate, blood vessel elasticity, the occurrence or non-occurrence of cardiovascular disease, or oxygen saturation, on the application program screen.

Additionally, the main driving circuit 200 may generate digital video data corresponding to touch coordinates according to touch coordinate data from the touch driving circuit 400, or may execute an application indicated by an icon displayed on the user's touch coordinates.

Figure 6:
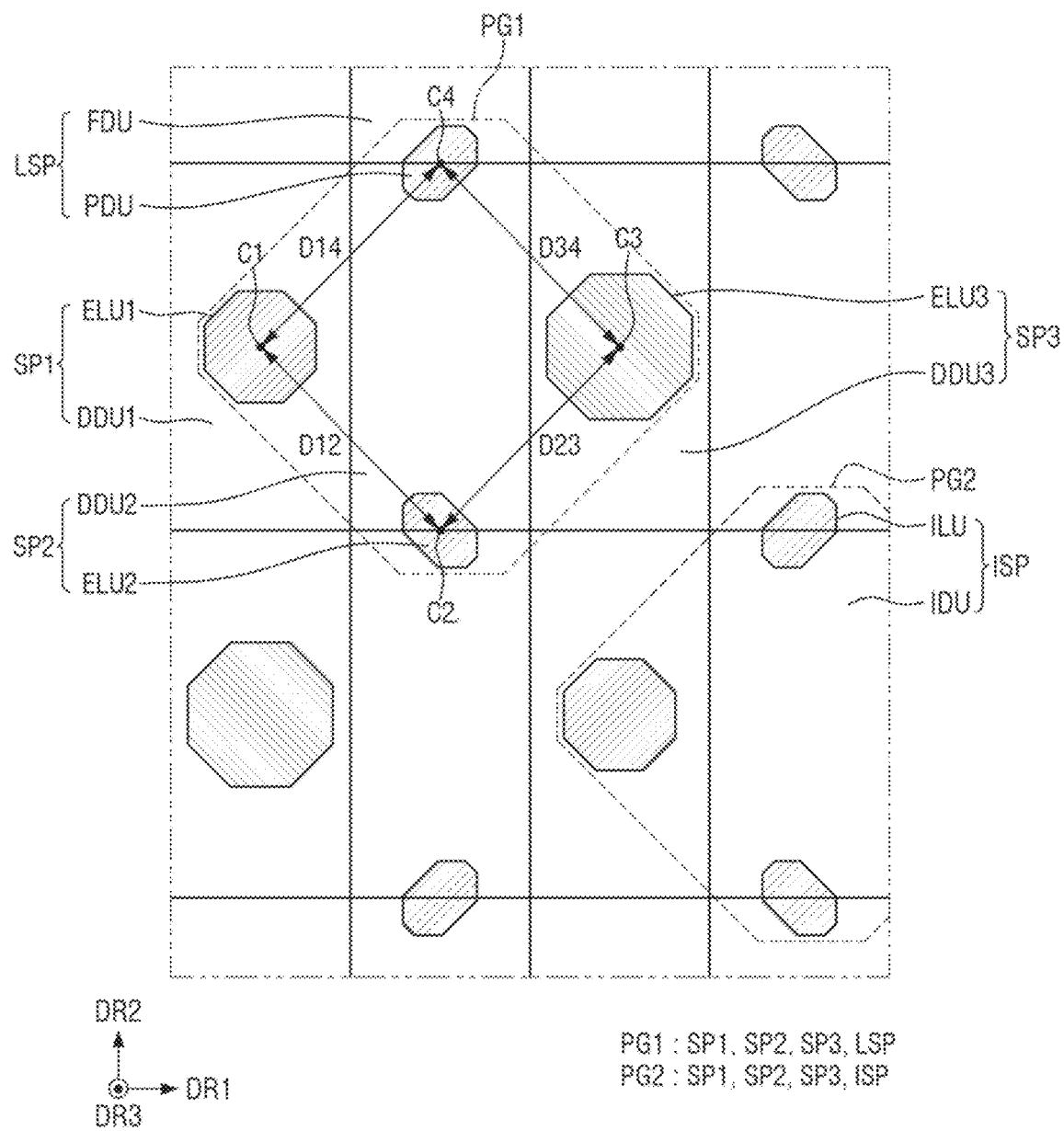
FIG. 6 is a layout diagram illustrating a display area according to one embodiment.

FIG. 6 is a layout diagram illustrating a display area according to one embodiment.

Referring to FIG. 6, the display area DA may include the display pixels SP, infrared light emitting pixels ISP, and the light sensing pixels LSP. Here, the display pixels SP may be divided into the first display pixels SP1, the second display pixels SP2, and the third display pixels SP3.

The light sensing pixel LSP, the first display pixel SP1, the second display pixel SP2, and the third display pixel SP3 may be referred to as a first unit pixel PG1. Further, the infrared light emitting pixel ISP, the first display pixel SP1, the second display pixel SP2, and the third display pixel SP3 may be referred to as a second unit pixel PG2.

The first and second unit pixels PG1 and PG2 may be a minimum unit display pixels capable of displaying white, and each first unit pixel PG1 may sense light. The first unit pixels PG1 and the second unit pixels PG2 may be alternately arranged in a zigzag shape in a plan view, and may be arranged in a matrix form in one diagonal direction. Further, the first unit pixels PG1 and the second unit pixels PG2 may be alternately arranged in horizontal or vertical stripes in a matrix form in a plan view.

The first display pixel SP1 may include a first light emitting portion ELU1 that emits first light, and a first pixel driver DDU1 for applying a driving current to the light emitting element of the first light emitting portion ELU1. The first light may be light of a red wavelength band. For example, the main peak wavelength of the first light may be located at approximately 600 nm to 750 nm.

The second display pixel SP2 may include a second light emitting portion ELU2 that emits second light, and a second pixel driver DDU2 for applying a driving current to the light emitting element of the second light emitting portion ELU2. The second light may be light of a blue wavelength band. For example, the main peak wavelength of the third light may be located at approximately 370 nm to 460 nm.

The third display pixel SP3 may include a third light emitting portion ELU3 that emits third light, and a third pixel driver DDU3 for applying a driving current to the light emitting element of the third light emitting portion ELU3. The third light may be light of a blue wavelength band. For example, the third light may be light of a green wavelength band. For example, the main peak wavelength of the second light may be located at approximately 480 nm to 560 nm.

The infrared light emitting pixel ISP may include an infrared light emitting portion ILU emitting light of an infrared wavelength band and an infrared light pixel driver LDU for applying a driving current to the light emitting element of the infrared light emitting portion ILU. The main peak wavelength of the infrared light may be located at approximately 750 nm to 1 mm.

The light sensing pixel LSP includes a light sensing portion PDU and a sensing driver FDU.

In the first unit pixel GP1, the first to third pixel drivers DDU1 to DDU3 may be arranged in a preset order in the first direction DR1. Alternatively, any one of the first to third pixel drivers DDU1 to DDU3 may be disposed in the first direction DR1 of another adjacent pixel driver. Further, the sensing driver FDU may be disposed in the first direction DR1 of any one of the first to third pixel drivers DDU1 to DDU3. Alternatively, the sensing driver FDU may be disposed in the second direction DR2 of any one of the first to third pixel drivers DDU1 to DDU3.

The first pixel drivers DDU1 adjacent to each other in the data line DL direction may be disposed in the second direction DR2. The second pixel drivers DDU2 adjacent to each other in the direction of the data line DL may be disposed in the second direction DR2. Similarly, all the sensing drivers FDU adjacent to each other in the direction of the data line DL may also be disposed in the second direction DR2.

The first light emitting portion ELU1, the second light emitting portion ELU2, the third light emitting portion ELU3, the infrared light emitting portion ILU, and the light sensing portion PDU may have a rectangular, octagonal, or rhombic planar shape, but the present disclosure is not limited thereto. The first light emitting portion ELU1, the second light emitting portion ELU2, the third light emitting portion ELU3, the infrared light emitting portion ILU, and the light sensing portion PDU may have another polygonal planar shape other than a rectangle, an octagon, and a rhombus.

On the other hand, due to the arrangement position and planar shape of the first light emitting portion ELU1, the second light emitting portion ELU2, the third light emitting portion ELU3, and the light sensing unit PDU, a distance D12 between a center C1 of the first light emitting portion ELU1 and a center C2 of the second light emitting portion ELU2 adjacent to each other, a distance D23 between the center C2 of the second light emitting portion ELU2 and a center C3 of the third light emitting portion ELU3 adjacent to each other, a distance D14 between the center C1 of the first light emitting unit ELU1 and a center C2 of the second light emitting portion ELU2 adjacent to each other in another direction, and a distance D34 between a center C4 of the second light emitting portion ELU2 and the center C3 of the third light emitting portion ELU3 may be substantially the same.

Figure 7:
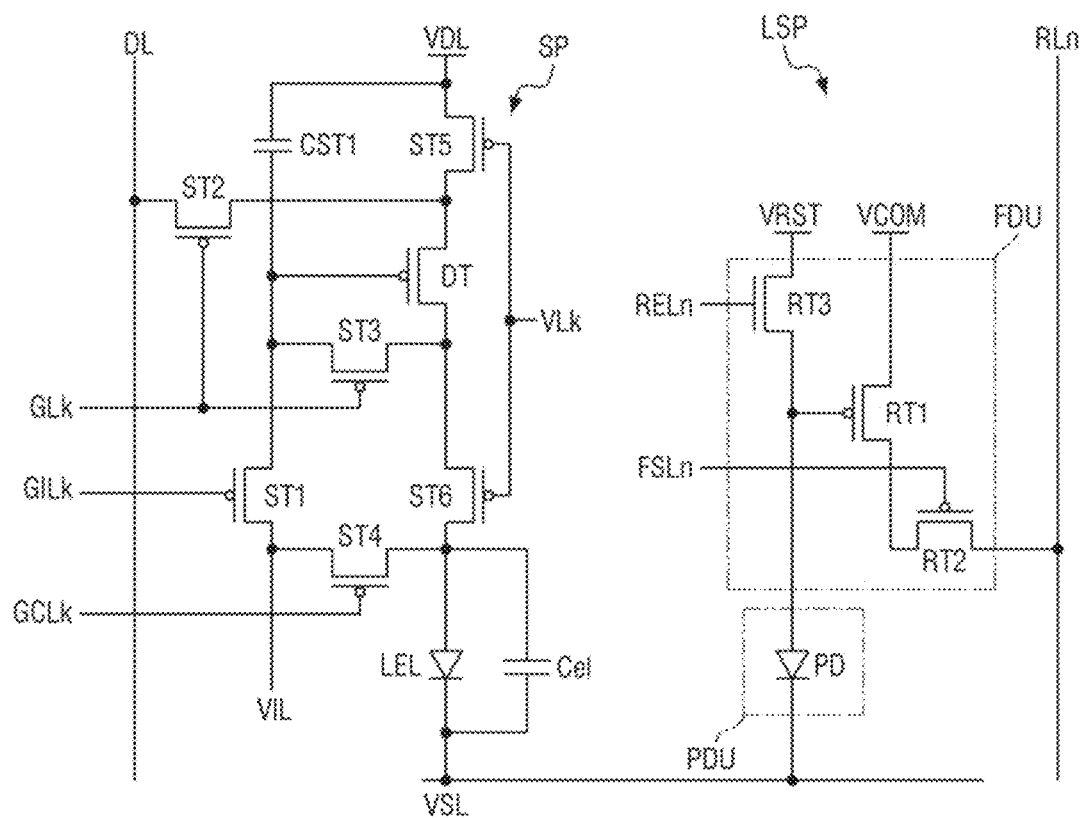
FIG. 7 is a circuit diagram illustrating a display pixel and a light sensing pixel according to one embodiment.

FIG. 7 is a circuit diagram illustrating a display pixel and a light sensing pixel according to one embodiment.

Referring to FIG. 7, each display pixel according to one embodiment may be connected to a $k^{th}$ display initialization line GILk, a $k^{th}$ display scan line GLk, a $k^{th}$ display control line GCLk, and a $k^{th}$ emission control line VLk. In addition, the display pixel SP may be connected to a first driving voltage line VDL to which a first driving voltage is supplied, a second driving voltage line VSL to which a second driving voltage is supplied, and a third driving voltage line VIL to which a third driving voltage is supplied. Hereinafter, k, n and the like may be used in place of numbers are positive integers excluding 0.

The display pixel SP may include a light emitting portion ELU and a pixel driver DDU. The light emitting portion ELU may include a light emitting element LEL. The pixel driver DDU may include a driving transistor DT, switch elements, and a capacitor CST1. The switch elements include the first to sixth transistors ST1, ST2, ST3, ST4, ST5, and ST6.

The driving transistor DT may include a gate electrode, a first electrode, and a second electrode. The driving transistor DT controls a drain-source current Ids (hereinafter, referred to as "driving current") flowing between the first electrode and the second electrode according to a data voltage applied to the gate electrode. The driving current Ids flowing through a channel of the driving transistor DT is proportional to the square of the difference between a threshold voltage and a voltage Vsg between the first electrode and the gate electrode of the driving transistor DT, as shown in Eq. (1).

$$Ids = k' \times (Vsg - Vth)^2 \qquad (1)$$

In Eq. (1), k' is a proportional coefficient determined by the structure and physical characteristics of the driving transistor, Vsg is a voltage between the first electrode and the gate electrode of the driving transistor, and Vth is a threshold voltage of the driving transistor.

The light emitting element LEL emits light by the driving current Ids. As the driving current Ids increases, the amount of light emitted from the light emitting element LEL may increase.

The light emitting element LEL may be an organic light emitting diode including an organic light emitting layer disposed between an anode electrode and a cathode electrode. Alternatively, the light emitting element LEL may be an inorganic light emitting element including an inorganic semiconductor disposed between an anode electrode and a cathode electrode. Alternatively, the light emitting element LEL may be a quantum dot light emitting element including a quantum dot light emitting layer disposed between an anode electrode and a cathode electrode. Alternatively, the light emitting element LEL may be a micro light emitting element including a micro light emitting diode disposed between an anode electrode and a cathode electrode.

The anode electrode of the light emitting element LEL may be connected to a first electrode of the fourth transistor ST4 and a second electrode of the sixth transistor ST6, and the cathode electrode of the light emitting element LEL may be connected to the second driving voltage line VSL. A parasitic capacitance Cel may be formed between the anode electrode and the cathode electrode of the light emitting element LEL.

The first transistor ST1 is turned on by a display initialization signal of the $k^{th}$ display initialization line GILk to connect the gate electrode of the driving transistor DT to the third driving voltage line VIL. Accordingly, the third driving voltage VINT of the third driving voltage line VIL may be applied to the gate electrode of the driving transistor DT. The gate electrode of the first transistor ST1 may be connected to the $k^{th}$ display initialization line GILk, the first electrode of the first transistor ST1 may be connected to the gate electrode of the driving transistor DT, and the second electrode of the first transistor ST1 may be connected to the third driving voltage line VIL.

The second transistor ST2 is turned on by a display scan signal of the $k^{th}$ display scan line GLk to connect the first electrode of the driving transistor DT to the data line DL. Accordingly, the data voltage of the data line DL may be applied to the first electrode of the driving transistor DT. The gate electrode of the second transistor ST2 may be connected to the $k^{th}$ display scan line GLk, the first electrode of the second transistor ST2 may be connected to the first electrode of the driving transistor DT, and the second electrode of the second transistor ST2 may be connected to the data line DL.

The third transistor ST3 is turned on by a display scan signal of the $k^{th}$ display scan line GLk to connect the gate electrode of the driving transistor DT to the second electrode of the third transistor ST3. When the gate electrode of the driving transistor DT is connected to the second electrode of third transistor ST3, the driving transistor DT is driven as a diode. The gate electrode of the third transistor ST3 may be connected to the k$^{th}$ display scan line GLk, the first electrode of the third transistor ST3 may be connected to the second electrode of the driving transistor DT, and the second electrode of the third transistor ST3 may be connected to the gate electrode of the driving transistor DT.

The fourth transistor ST4 is turned on by the display control signal of the k$^{th}$ display control line GCLk to connect the anode electrode of the light emitting element LEL to the third driving voltage line VIL. The third driving voltage of the third driving voltage line VIL may be applied to the anode electrode of the light emitting element LEL. The gate electrode of the fourth transistor ST4 is connected to the k$^{th}$ display control line GCLk, the first electrode of the fourth transistor ST4 is connected to the anode electrode of the light emitting element LEL, and the second electrode of the fourth transistor ST4 is connected to the third driving voltage line VIL.

The fifth transistor ST5 is turned on by an emission signal of the k$^{th}$ emission control line VLk to connect the first electrode of the driving transistor DT to the first driving voltage line VDL. The gate electrode of the fifth transistor ST5 is connected to the k$^{th}$ emission control line VLk, the first electrode of the fifth transistor ST5 is connected to the first driving voltage line VDL, and the second electrode of the fifth transistor ST5 is connected to the first electrode of the driving transistor DT.

The sixth transistor ST6 is disposed between the second electrode of the driving transistor DT and the anode electrode of the light emitting element LEL. The sixth transistor ST6 is turned on by the emission control signal of the k$^{th}$ emission control line VLk to connect the second electrode of the driving transistor DT to the anode electrode of the light emitting element LEL. The gate electrode of the sixth transistor ST6 is connected to the k$^{th}$ emission control line VLk, the first electrode of the sixth transistor ST6 is connected to the second electrode of the driving transistor DT, and the second electrode of the sixth transistor ST6 is connected to the anode electrode of the light emitting element LEL.

When both the fifth transistor ST5 and the sixth transistor ST6 are turned on, the driving current Ids of the driving transistor DT according to the data voltage applied to the gate electrode of the driving transistor DT may flow to the light emitting element LEL.

The capacitor CST1 is formed between the gate electrode of the driving transistor DT and the first driving voltage line VDL. The first capacitor electrode of the capacitor CST1 may be connected to the gate electrode of the driving transistor DT, and the second capacitor electrode of the capacitor CST1 may be connected to the first driving voltage line VDL.

When the first electrode of each of the driving transistor DT and the first to sixth transistors ST1 to ST6 is a source electrode, the second electrode of each of the driving transistor DT and the first to sixth transistors ST1 to ST6 may be a drain electrode. Alternatively, when the first electrode of each of the driving transistor DT and the first to sixth transistors ST1 to ST6 is a drain electrode, the second electrode of each of the driving transistor DT and the first to sixth transistors ST1 to ST6 may be a source electrode.

An active layer of each of the driving transistor DT and the first to sixth transistors ST1 to ST6 may be formed of any one of polysilicon, amorphous silicon, or an oxide semiconductor. In FIG. 7, the first to sixth transistors ST1 to ST6, and the driving transistor DT have been mainly described as being formed of a P-type metal oxide semiconductor field effect transistor (MOSFET), but the present disclosure is not limited thereto. For example, the first to sixth transistors ST1 to ST6, and the driving transistor DT may be formed of an N-type MOSFET. Alternatively, at least one of the first to sixth transistors ST1 to ST6 may be formed of an N-type MOSFET.

The light sensing pixels LSP are respectively electrically connected to an n$^{th}$ sensing reset line RSLn, an n$^{th}$ light sensing scan line FSLn, and an n$^{th}$ light sensing line RLn. Each of the light sensing pixels LSP may be reset by a reset signal from the n$^{th}$ sensing reset line RSLn, and may transmit a light sensing signal to each n$^{th}$ light sensing line RLn in response to a sensing scan signal from the n$^{th}$ light sensing scan line FSLn.

The light sensing pixels LSP may be divided into the light sensing portion PDU including a light sensing element PD, and the sensing driver FDU including first to third sensing transistors RT1 to RT3 and a sensing capacitor. Here, the sensing capacitor may be formed in parallel with the light sensing element PD.

The first sensing transistor RT1 of the sensing driver FDU may allow a light sensing current to flow according to the voltages of the light sensing element PD and the sensing capacitor. The amount of the light sensing current may vary depending on a voltage applied to the light sensing element PD and the sensing capacitor. The gate electrode of the first sensing transistor RT1 may be connected to the second electrode of the light sensing element PD. The first electrode of the first sensing transistor RT1 may be connected to a common voltage source Vcom to which a common voltage is applied. The second electrode of the first sensing transistor RT1 may be connected to the first electrode of the second sensing transistor RT2.

When a sensing scan signal of a gate-on voltage is applied to the n$^{th}$ light sensing scan line FSLn, the second sensing transistor RT2 may allow a sensing current of the first sensing transistor RT1 to flow to the n$^{th}$ light sensing line RLn. In this case, the n$^{th}$ light sensing line RLn may be charged with a sensing voltage by the sensing current. The gate electrode of the second sensing transistor RT2 may be connected to the n$^{th}$ light sensing scan line FSLn, the first electrode of the second sensing transistor RT2 may be connected to the second electrode of the first sensing transistor RT1, and the second electrode of the second sensing transistor RT2 may be connected to the n$^{th}$ light sensing line RLn.

When a reset signal of the gate-on voltage is applied to the n$^{th}$ sensing reset line RSLn, the third sensing transistor RT3 may reset the voltages of the light sensing element PD and the sensing capacitor to a reset voltage of a reset voltage source VRST. The gate electrode of the third sensing transistor RT3 may be connected to the sensing reset line RSL, the first electrode of the third sensing transistor RT3 may be connected to the reset voltage source VRST, and the second electrode of the third sensing transistor RT3 may be connected to the second electrode of the light sensing element PD.

It is illustrated in FIG. 7 that the first sensing transistor RT1 and the second sensing transistor RT2 are formed of a P-type MOSFET, and the third sensing transistor RT3 is formed of an N-type MOSFET. However, an embodiment of the present disclosure is not limited thereto, and they may be selectively formed in the same type or different types. Further, any one of the first electrode and the second electrode of each of the first sensing transistor RT1, the second sensing transistor RT2, and the third sensing transistor RT3 may be the source electrode and the other one may be the drain electrode.

Figure 8:
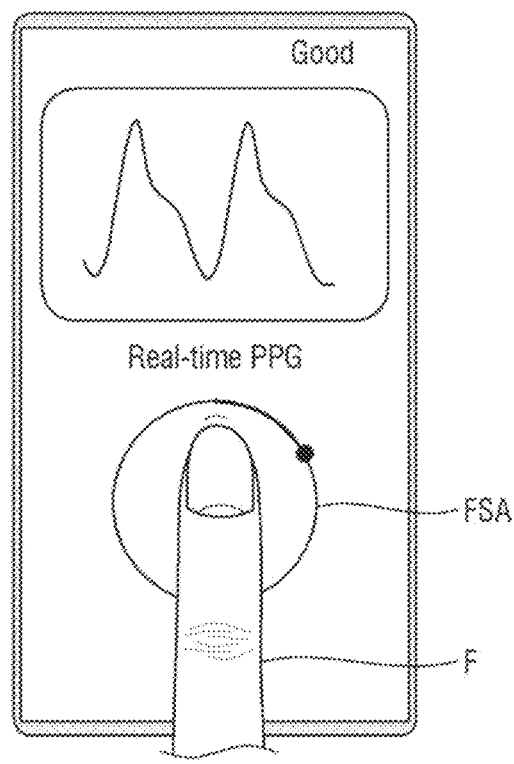
FIG. 8 is a diagram showing an image display screen and a body part touch area detection process during a biometric information measurement period.

FIG. 8 is a diagram showing an image display screen and a body part touch area detection process during a biometric information measurement period.

Referring to FIG. 8, during the biometric information detection period, the main driving circuit 200 supplies the data voltage to the first and second unit pixels PG1 and PG2 of the display panel 100, and supplies the control signals to the display scan driver 110 and the light sensing scan driver 120 to display a preset application program screen for pulse wave signal detection in the display area DA.

The main driving circuit 200 displays the touch sensing area FSA where a touch of a body part, such as a finger F or the like, is sensed on the application program screen, and displays the waveforms of the pulse wave signals detected in real time on the display window to guide the pulse wave signal detection process. At this time, the main driving circuit 200 displays a period required for biometric information measurement, a pulse wave signal detection period, and the body part touch sensing area FSA in the form of a circular or bar graph on the application program screen. For example, the main driving circuit 200 displays the time required for measuring biometric information, the pulse wave signal detection period, and the body part touch sensing area FSA, either in the form of a circular or bar graph, on the application program screen.

During the biometric information detection period, the main driving circuit 200 receives touch position coordinates sensed by the touch sensing unit TSU or the pressure sensing unit PSU using the touch driving circuit 400. Then, the main driving circuit 200 supplies the data voltage to the first and second unit pixels PG1 and PG2 arranged at the portion of the touch sensing area FSA that is touched by the finger F, and supplies the control signals to the display scan driver 110 and the light sensing scan driver 120. At this time, the main driving circuit 200 may supply a preset data voltage to at least one of the first and second display pixels SP1 and SP2 included in the first and second unit pixels PG1 and PG2, so that an optical signal may be detected by at least one of the green light or the red light. Thereafter, the main driving circuit 200 receives the optical signals, in other words, the light sensing signals, from the light sensing pixels LSP through the light sensing lines ERL of the display panel 100.

The main driving circuit 200 detects the pulse wave signals (PPG signals) corresponding to the light sensing signals received in real time and stores them as digital signal data. The pulse wave signals correspond to the magnitudes of the light sensing signals and the changes in those magnitudes. The main driving circuit 200 displays the pulse wave signals detected in real time on the display window of the application program screen in a graphic form of a graph type.

Figure 9:
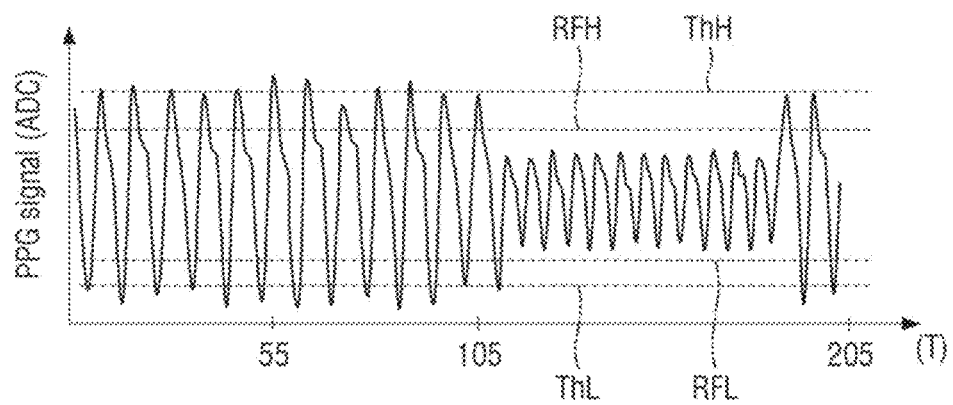
FIG. 9 is a graph showing a pulse wave signal detected in real time during a biometric information measurement period and an inaccurate pulse wave signal detection process.

FIG. 9 is a graph showing a pulse wave signal detected in real time during a biometric information measurement period and an inaccurate pulse wave signal detection process.

Referring to FIG. 9, the main driving circuit 200 performs preset signal processing processes for light sensing signals, such as amplification, filtering, and sampling of the light sensing signals detected by the light sensing pixels LSP at a position where a body part, such as the finger F or the like, is touched. Then, the pulse wave signals PPG corresponding to the magnitudes of the signal-processed light sensing signals and the changes in those magnitudes are generated, stored in units of preset periods, and monitored.

The main driving circuit 200 analyzes the high pulse magnitude change and the low pulse magnitude change of the pulse wave signals PPG generated and stored in real time, and calculates an average magnitude value RFH of high pulses and an average magnitude value RFL of low pulses in real time. Then, the main driving circuit 200 sets a normal pulse wave signal detection period or an inaccurate pulse wave signal detection period in real time according to a comparison result of the average magnitude value RFH of high pulses to a preset high threshold ThH and the average magnitude value RFL of low pulses to a preset low threshold ThL.

For example, the main driving circuit 200 sets the normal pulse wave signal detection period when the average magnitude value RFH of high pulses is greater than or equal to the preset high threshold ThH during a plurality of preset frame periods. Further, the main driving circuit 200 may set the normal pulse wave signal detection period when the average magnitude value RFL of low pulses is the preset low threshold ThL during a plurality of preset frame periods.

Alternatively, the main driving circuit 200 sets the inaccurate pulse wave signal detection period when the average magnitude value RFH of high pulses is smaller than the preset high threshold ThH during a plurality of preset frame periods. Further, the main driving circuit 200 may set the inaccurate pulse wave signal detection period when the average magnitude value RFL of low pulses is smaller than the preset low threshold ThL during a plurality of preset frame periods.

Figure 10:
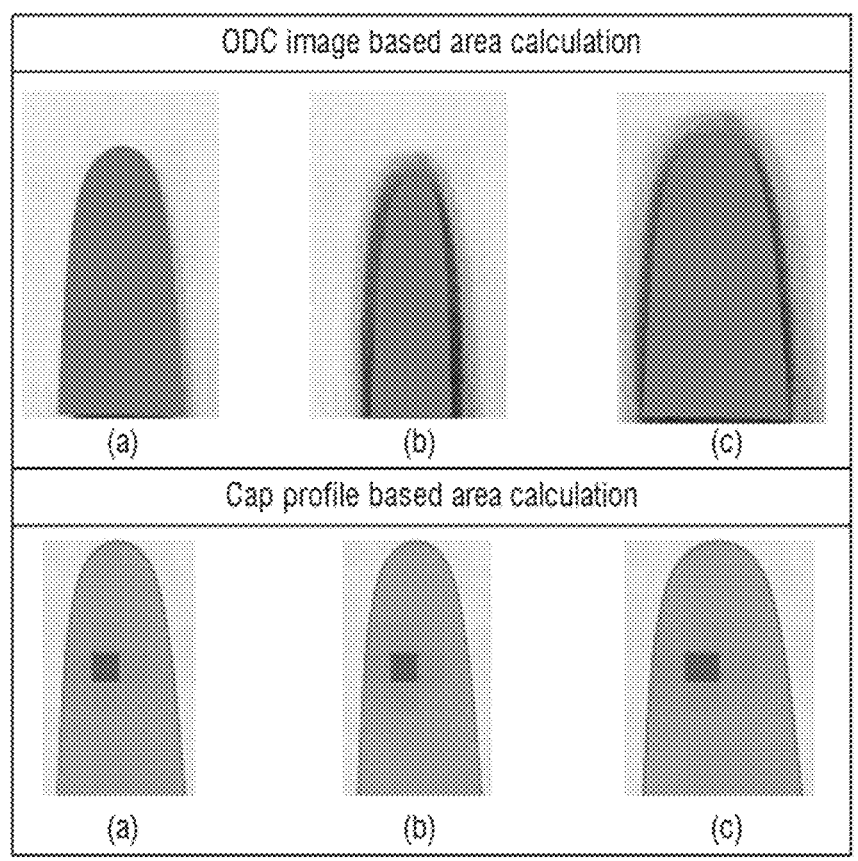
FIG. 10 is an image diagram showing a detection process of inaccurately detecting a pulse wave signal during a biometric information measurement period.

FIG. 10 is an image diagram showing a detection process of inaccurately detecting a pulse wave signal during a biometric information measurement period.

Referring to FIG. 10, the main driving circuit 200 performs preset signal processing processes on light sensing signals detected by the light sensing pixels LSP of a position where a body part, such as the finger F or the like, is touched. Further, an image (ODC image) based on the signal value detected by the light sensing pixels LSP is generated. Then, a touch area or a touch shape is analyzed based on the signal values and the image detected by the light sensing pixels LSP. When the touch area is smaller than a reference area, the inaccurate pulse wave signal detection period may be set.

Alternatively, the main driving circuit 200 generates a capacitance (Cap) profile for signal values based on the signal values detected by the light sensing pixels LSP. Further, the touch area or the touch shape is analyzed based on the signal values and the image detected by the light sensing pixels LSP. Then, the touch area or the touch shape is analyzed based on the Cap profile detected by the light sensing pixels LSP. When the touch area is smaller than the reference area, the inaccurate pulse wave signal detection period may be set.

Figure 11:
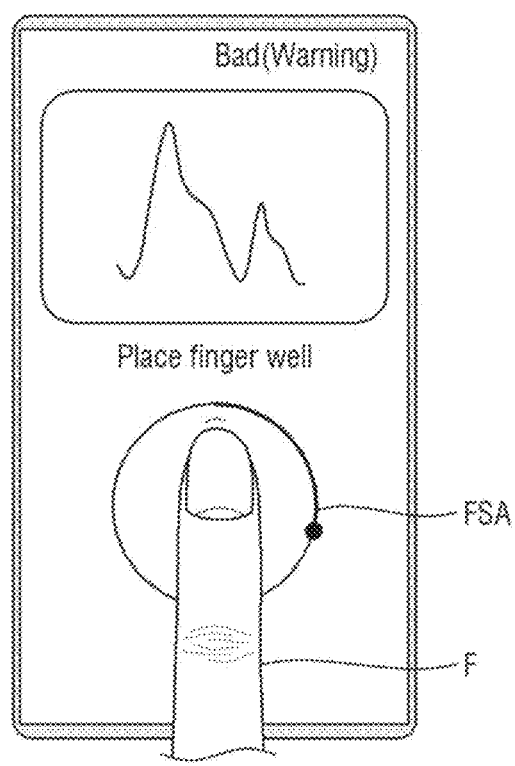
FIG. 11 is a diagram showing an image display screen displayed when an inaccurate pulse wave signal is detected during a biometric information measurement period.

FIG. 11 is a diagram showing an image display screen displayed when an inaccurate pulse wave signal is detected during a biometric information measurement period.

As shown in FIG. 11, the main driving circuit 200 displays the waveforms of the pulse wave signals detected in real time, as a graphic screen, on the display window of the application program. This way, a user may check the pulse wave signal detected in real time during the biometric information detection period.

The main driving circuit 200 displays a touch guide message on the application program screen so that a body part, such as the finger F or the like, may be accurately touched and the touch state may be maintained during the inaccurate pulse wave signal detection period. At this time, the pulse wave signal and the touch guide message displayed in real time may be changed and displayed as a warning color such as red or the like.

Then, when the normal pulse wave signal detection period is set according to the detection result of the average magnitude value RFH of high pulses and the average magnitude value RFL of low pulses, the main driving circuit 200 displays the normal touch guide message on the application program screen so that the normal touch state may be maintained. At this time, the pulse wave signal and the touch guide message displayed in real time may be changed and displayed as a normal color such as green, blue, or the like.

Figure 12:
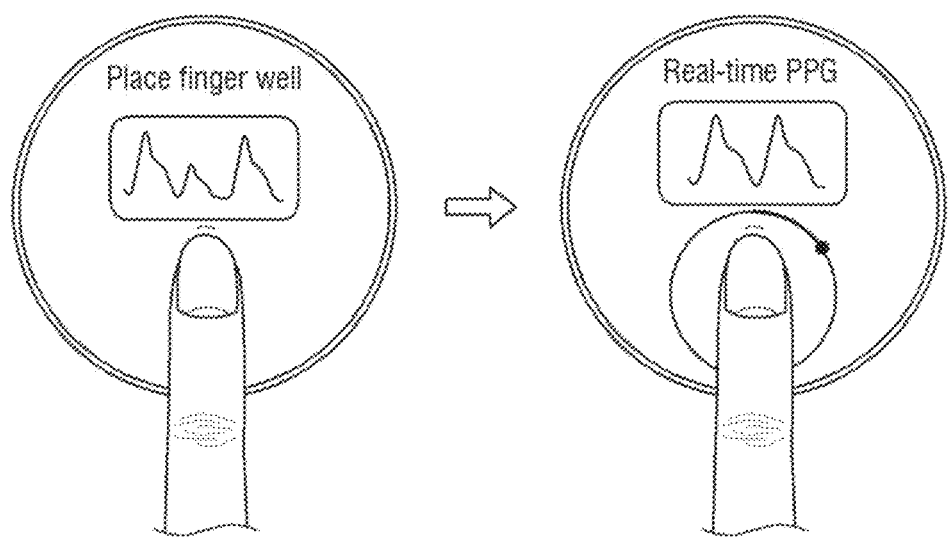
FIG. 12 is a diagram showing a biometric information measuring method using a watch type display device and an image display screen.

FIG. 12 is a diagram showing a biometric information measuring method using a watch type display device and an image display screen.

As shown in FIGS. 8 and 11, the display device 10 for measuring biometric information such as blood pressure, heart rate, heart rate variability, respiratory rate, blood vessel elasticity, cardiovascular disease, oxygen saturation, and the like may be applied to a mobile communication terminal such as a smart phone, a tablet display device, or the like. On the other hand, as shown in FIG. 12, the display device 10 for measuring biometric information according to an embodiment of the present disclosure may be equally applied to a wearable device such as a smart watch, a watch phone, or the like.

Figure 14:
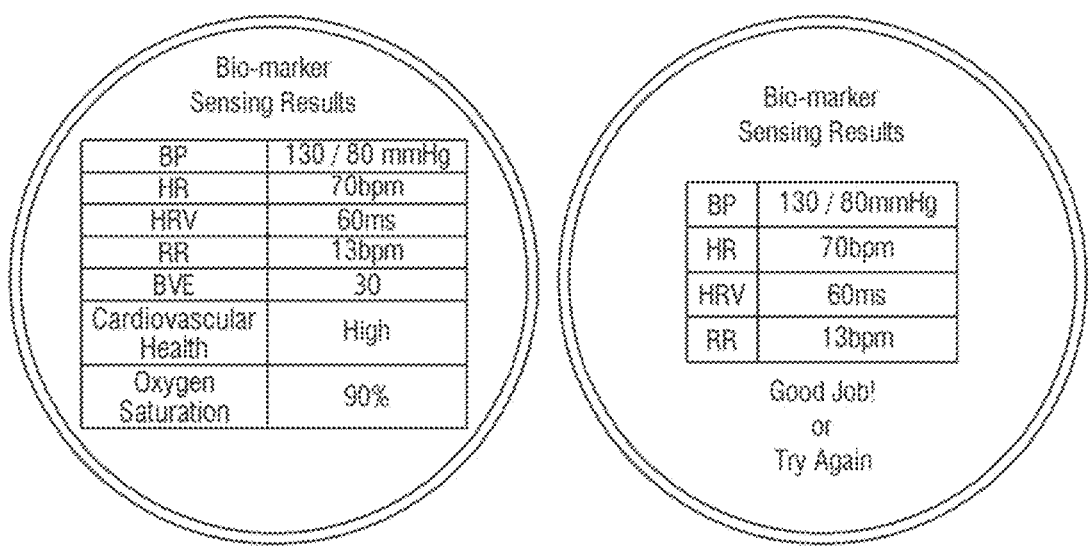
FIG. 14 is a diagram showing biometric information measurement results obtained using a watch type display device.

FIG. 13 is a diagram showing biometric information measurement results obtained using a mobile display device. FIG. 14 is a diagram showing biometric information measurement results obtained using a watch type display device.

Referring to FIGS. 13 and 14, the display device 10 applied to a mobile communication terminal or a wearable device may display an application program for measuring biometric information in the display area DA according to the user's selection, and may be switched to a biometric information measurement mode through the application program.

The main driving circuit 200 may set the normal pulse wave signal detection period or the inaccurate pulse wave signal detection period in real time by checking and analyzing the magnitude change of high pulses and low pulses of the pulse wave signals PPG during the biometric information measurement period. In particular, the main driving circuit 200 induces accurate touch by displaying the touch guide message on the application program screen so that a body part, such as the finger F or the like, may be accurately touched and the touch state may be maintained during the inaccurate pulse wave signal detection period.

The main driving circuit 200 analyzes various aspects of the detected pulse wave signals PPG during the normal pulse wave signal detection period. For example, main driving circuit 200 analyzes the high pulse cycle and the changes in the high pulse cycle, the magnitude of the high pulse and its changes, the magnitude of the low pulse and its changes, changes in the signal waveform, the period in which a high pulse reaches its peak, and the difference in the pulse magnitude of the pulse wave signals PPG respectively detected by green light and red light, among others. Then, the biometric information such as a blood pressure BP, a heart rate HR, heart rate variability HRV, a respiratory rate RR, blood vessel elasticity BVE, a cardiovascular disease (or, a cardiovascular health analysis result score), oxygen saturation, or the like is obtained according to the analysis result, and the obtained result is displayed on the application program screen.

Figure 15:
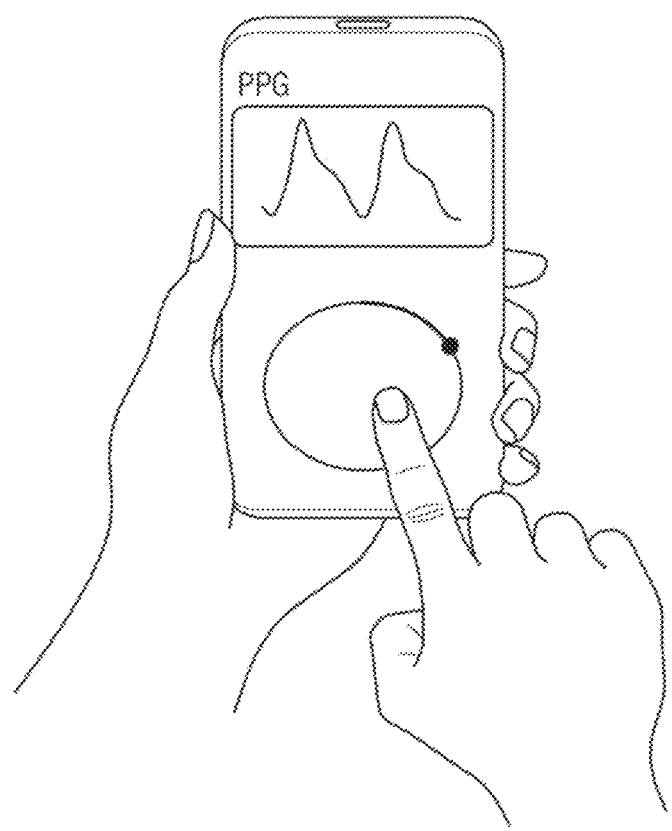
FIG. 15 is a diagram showing a biometric information measuring method using a mobile display device and an image display screen.
Figure 16:
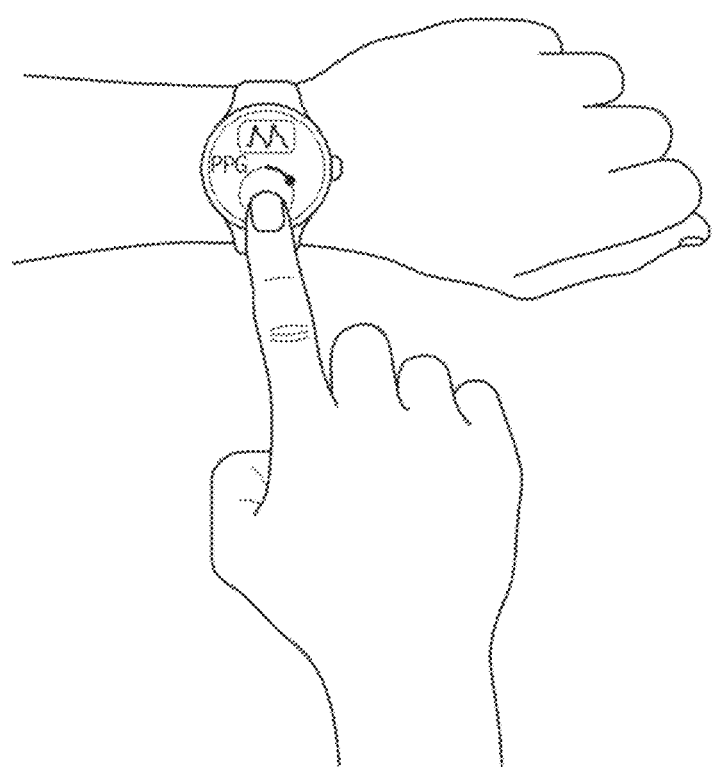
FIG. 16 is a diagram showing a biometric information measuring method using a watch type display device and an image display screen.
Figure 17:
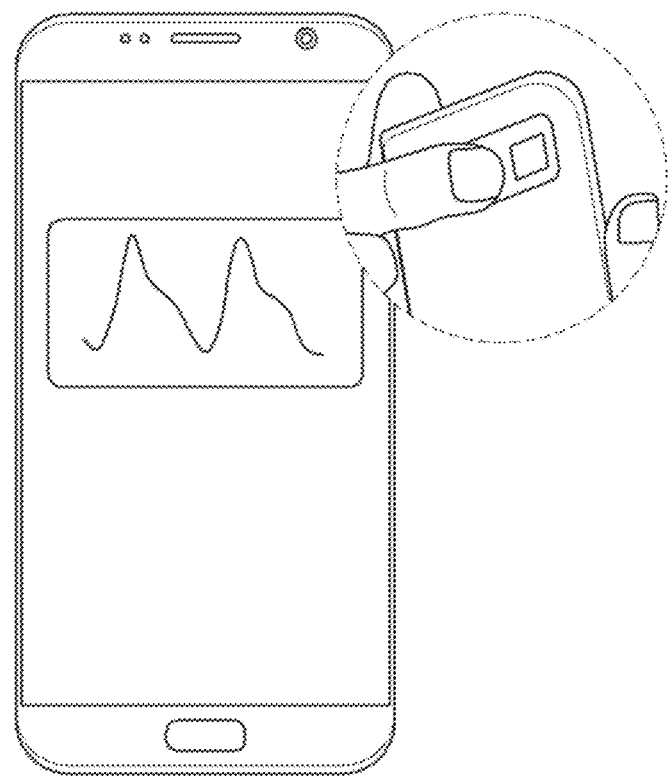
FIG. 17 is a diagram showing a method for measuring biometric information in a touch sensing area formed on a rear surface of a mobile display device and an image display screen.
Figure 18:
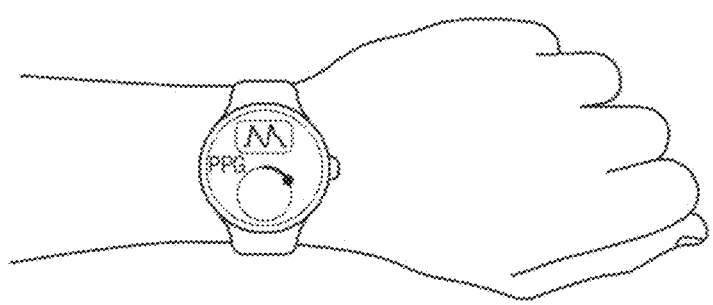
FIG. 18 is a diagram showing a method for measuring biometric information at a wrist using a watch type display device.
Figure 19:
FIG. 19 is a diagram showing a biometric information measuring method using light reflected from a face.

FIG. 15 is a diagram showing a biometric information measuring method using a mobile display device and an image display screen. FIG. 16 is a diagram showing a biometric information measuring method using a watch type display device and an image display screen. FIG. 17 is a diagram showing a method for measuring biometric information in a touch sensing area formed on a rear surface of a mobile display device and an image display screen. FIG. 18 is a diagram showing a method for measuring biometric information at a wrist using a watch type display device. FIG. 19 is a diagram showing a biometric information measuring method using light reflected from a face.

Referring to FIGS. 15, 17, and 19, the display device 10 for measuring biometric information such as the blood pressure BP, the heart rate HR, the heart rate variability HRV, the respiratory rate RR, the blood vessel elasticity BVE, the cardiovascular disease (or the cardiovascular health analysis result score), the oxygen saturation, or the like may be applied to a mobile communication terminal such as a smart phone, a tablet display device, or the like. Further, as shown in FIGS. 16 and 18, the display device 10 for measuring biometric information may also be applied to a wearable device such as a smart watch, a watch phone, or the like.

Referring to FIGS. 15 and 16, the main driving circuits 200 of the display devices 10 respectively applied to the mobile display device and the watch type display device display the touch sensing area FSA touched by a body part such as the finger F or the like on the application program screen in the display area DA, and guides the pulse wave signal detection process. Further, the pulse wave signals of the body part that has touched the touch sensing area FSA of the display area DA may be respectively detected and stored as digital signal data. For example, the main driving circuit 200 of the mobile display device may store first pulse wave signals PPG detected by the touch sensing area FSA of the mobile display device as first digital signal data. On the other hand, the main driving circuit 200 of the watch type display device may store second pulse wave signals PPG detected by the touch sensing area FSA of the watch type display device as second digital signal data.

Further, referring to FIG. 17, the main driving circuit 200 may guide the pulse wave signal detection process by displaying the application program in the display area DA, and may detect the pulse wave signals of a body part that has touched the touch sensing area FSA formed on the rear surface of the display device 10 together with a video camera or the like. The main driving circuit 200 may also store third pulse wave signals PPG detected by the touch sensing area FSA formed on the rear surface of the display device 10 as third digital signal data.

Further, referring to FIG. 18, the main driving circuit 200 of the watch type display device may detect a light sensing signal and fourth pulse wave signals PPG at the user's wrist part by the detection area formed on the rear surface of the watch type display device. Then, the detected fourth pulse wave signals PPG may be stored as fourth digital signal data.

Further, referring to FIG. 19, the light sensing pixels LSP of the touch sensing area FSA may sense light reflected from the user's facial part and generate a light sensing signal, and the main driving circuit 200 may generate the third pulse wave signals PPG corresponding to the light sensing signal sensed by the light reflected from the facial part. Fifth pulse wave signals PPG may be stored as the fourth digital signal data.

Figure 20:
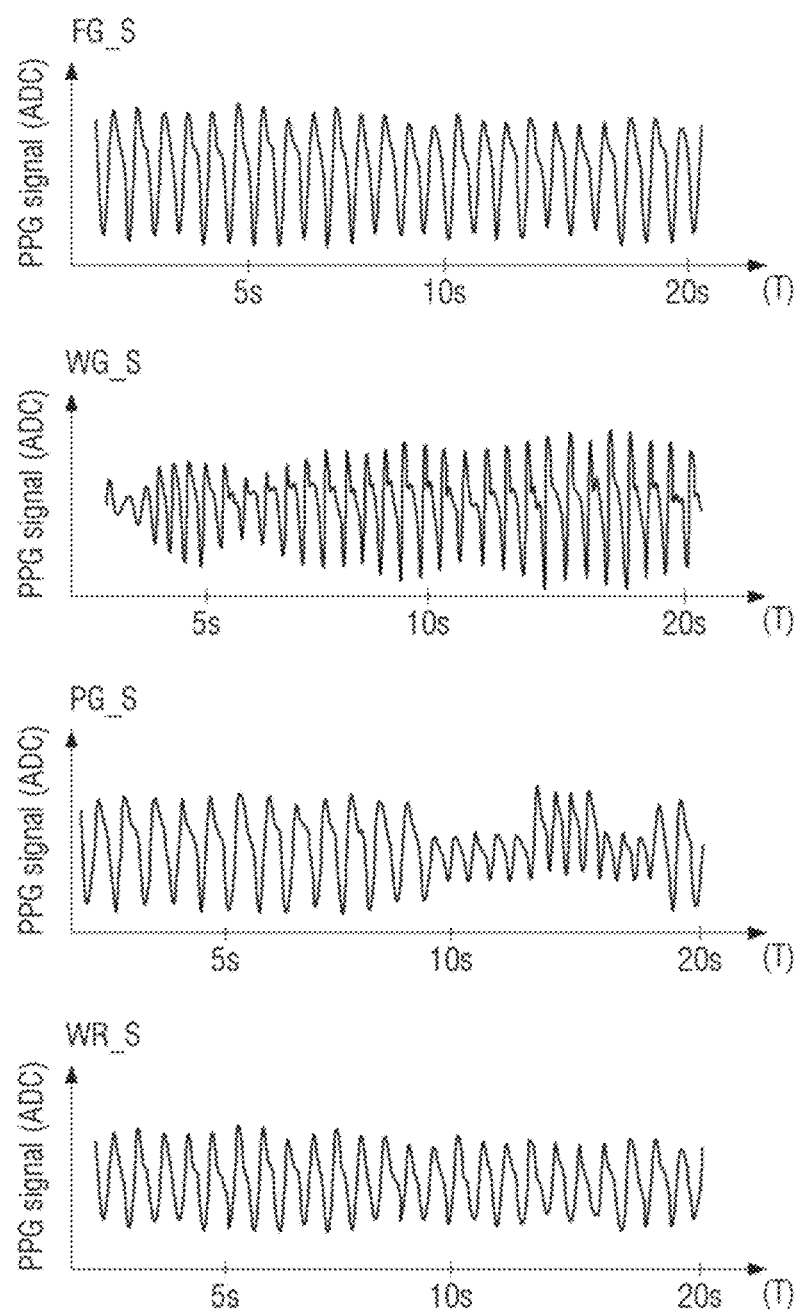
FIG. 20 is a graph showing a comparison of a mobile display device, a watch type display device, pulse wave signals detected in the touch sensing area on the rear surface of the mobile display device, and pulse wave signals detected in the detection area on the rear surface of the watch type display device.

FIG. 20 is a graph showing a comparison of a mobile display device, a watch type display device, pulse wave signals detected in the touch sensing area on the rear surface of the mobile display device, and pulse wave signals detected in the detection area on the rear surface of the watch type display device.

Referring to FIG. 20, the main driving circuit 200 formed at any one display device 10, such as a mobile display device or a watch type display device, receives the pulse wave signals PPG using the main driving circuits 200 of other display devices 10 connected by a short-distance wireless communication method such as Bluetooth, Wi-Fi, mirroring, or the like.

Referring to FIGS. 15 to 19 together with FIG. 20, any one main driving circuit 200 may receive the first to fifth digital signal data respectively including the first to fifth pulse wave signals PPG using other adjacent main driving circuits 200.

The main driving circuit 200 receives, compares, and analyzes at least two pulse wave signals among the first to fifth pulse wave signals received from the main driving circuit 200 of different display devices 10. Then, any one pulse wave signal PPG may be selected according to the analysis result to measure at least one piece of biometric information.

For example, the main driving circuit 200 may receive first pulse wave signals FG_S detected by the finger F that has touched the touch sensing area FSA of the display area DA, second pulse wave signals WG_S detected by the finger F that has touched the touch sensing area FSA of the watch type display device, third pulse wave signals PG_S detected by the touch sensing area FSA on the rear surface of the mobile display device, and fourth pulse wave signals WR_S detected by a wrist part that has touched the detection area on the rear surface of the watch type display device.

The main driving circuit 200 may calculate and compare the average magnitude value RFH of high pulses and the average magnitude value RFL of low pulses each of the first to fourth pulse wave signals FG_S, WG_S, PG_S, and WR_S. The main driving circuit 200 may then compare the first to fourth pulse wave signals FG_S, WG_S, PG_S, and WR_S with each other and select one of the first to fourth pulse wave signals FG_S, WG_S, PG_S, and WR_S according to the comparison result. Then, the selected pulse wave signal may be analyzed to obtain the biometric information such as the blood pressure BP, the heart rate HR, the heart rate variability HRV, the respiratory rate RR, the blood vessel elasticity BVE, the cardiovascular disease (or the cardiovascular health analysis result score), the oxygen saturation, or the like, and the obtained result may be displayed on the application program screen.

Alternatively, the main driving circuit 200 calculates the average magnitude value RFH of high pulses and the average magnitude value RFL of low pulses of the first to fourth pulse wave signals FG_S, WG_S, PG_S, and WR_S. Then, the calculated average magnitude value RFH of high pulses is compared with the preset high threshold ThH, and the average magnitude value RFL of low pulses is compared with the preset low threshold ThL. Then, any one of the first to fourth pulse wave signals FG_S, WG_S, PG_S, and WR_S may be selected according to the comparison result. Accordingly, the main driving circuit 200 may analyze the selected pulse wave signal to obtain the biometric information such as the blood pressure BP, the heart rate HR, the heart rate variability HRV, the respiratory rate RR, the blood vessel elasticity BVE, the cardiovascular disease (or the cardiovascular health analytical result score), the oxygen saturation, or the like, and may display the obtained result on the application program screen.

Figure 21:
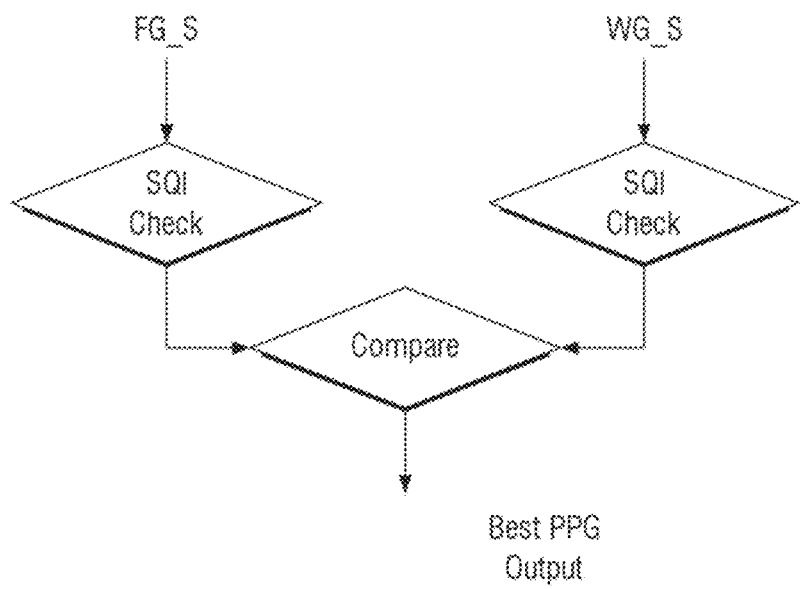
FIG. 21 is a flowchart illustrating a process of selecting a pulse wave signal for detecting biometric information by comparing pulse wave signals respectively detected in a mobile display device and a watch type display device.

FIG. 21 is a flowchart illustrating a process of selecting a pulse wave signal for detecting biometric information by comparing pulse wave signals respectively detected in a mobile display device and a watch type display device.

Referring to FIGS. 20 and 21, the main driving circuit 200 calculates the average magnitude value RFH of high pulses and the average magnitude value RFL of low pulses of the first to third pulse wave signals FG_S, WG_S, and PG_S that are respectively generated and calculated (SQl Check step). Then, the average magnitude values RFH of high pulses of the first to third pulse wave signals FG_S, WG_S, and PG_S are compared with each other to select any one pulse wave signal having the largest average magnitude value RFH of high pulses (Compare step). As an example, the first pulse wave signal FG_S that has the largest average magnitude value RFH of high pulses of the first to third pulse wave signals FG_S, WG_S, and PG_S may be selected. Alternatively, any one pulse wave signal having a median value among the average magnitude values RFH of high pulses that are compared with each other may be selected.

Alternatively, the main driving circuit 200 may compare the average magnitude values RFL of low pulses of the first to third pulse wave signals FG_S, WG_S, and PG_S with each other to select any one pulse wave signal having the smallest average magnitude value RFL of low pulses (Compare step). Alternatively, any one pulse wave signal having a median value may be selected among the average magnitude values RFL of low pulses that are compared with each other (Compare step).

Thereafter, the main driving circuit 200 may analyze the selected pulse wave signal to obtain the biometric information such as the blood pressure BP, the heart rate HR, the heart rate variability HRV, the respiratory rate RR, the blood vessel elasticity BVE, the cardiovascular disease (or the cardiovascular health analysis result score), the oxygen saturation, or the like, and may display the obtained result on the application program screen.

Figure 22:
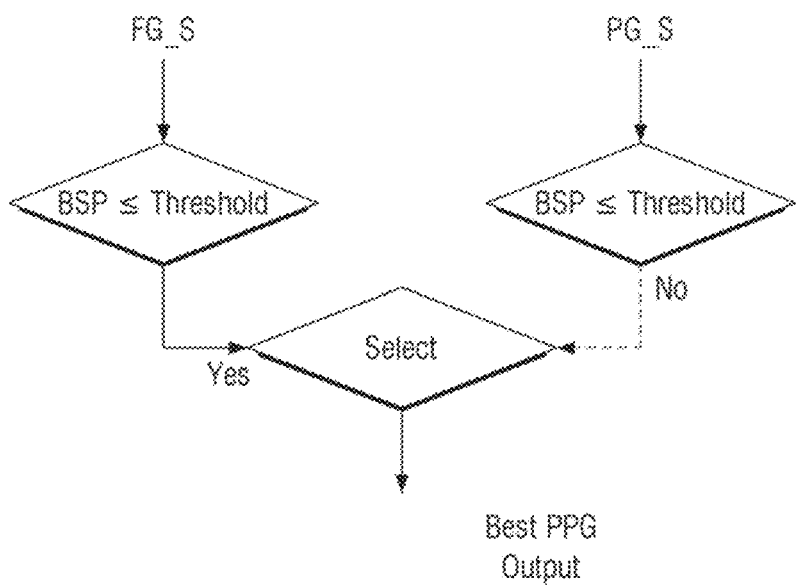
FIG. 22 is a flowchart illustrating a process of selecting a pulse wave signal for detecting biometric information among pulse wave signals respectively detected in the touch sensing areas on the front surface and the rear surface of a mobile display device.

FIG. 22 is a flowchart illustrating a process of selecting a pulse wave signal for detecting biometric information among pulse wave signals respectively detected in the touch sensing areas on the front surface and the rear surface of a mobile display device.

Referring to FIGS. 20 and 22, the main driving circuit 200 calculates the average magnitude value RFH of high pulses and the average magnitude value RFL of low pulses of the first to third pulse wave signals FG_S, WG_S, and PG_S that are respectively generated and received.

The main driving circuit 200 compares the average magnitude value RFH of high pulses calculated for each of the first to third pulse wave signals FG_S, WG_S, and PG_S with the preset high threshold ThH, and compares the average magnitude value RFL of low pulses with the preset low threshold ThL (BSP<Threshold step).

The main driving circuit 200 may select any one pulse wave signal having the largest average magnitude value RFH of high pulses compared to the preset high threshold ThH (Select step). Alternatively, any one pulse wave signal having the largest average magnitude value RFL of low pulses compared to the preset low threshold ThL may be selected (Select step).

The main driving circuit 200 may analyze the selected pulse wave signal to obtain the biometric information such as the blood pressure BP, the heart rate HR, the heart rate variability HRV, the respiratory rate RR, the blood vessel elasticity BVE, the cardiovascular disease (or the cardiovascular health analysis result score), the oxygen saturation, or the like, and may display the obtained result on the application program screen.

Figure 23:
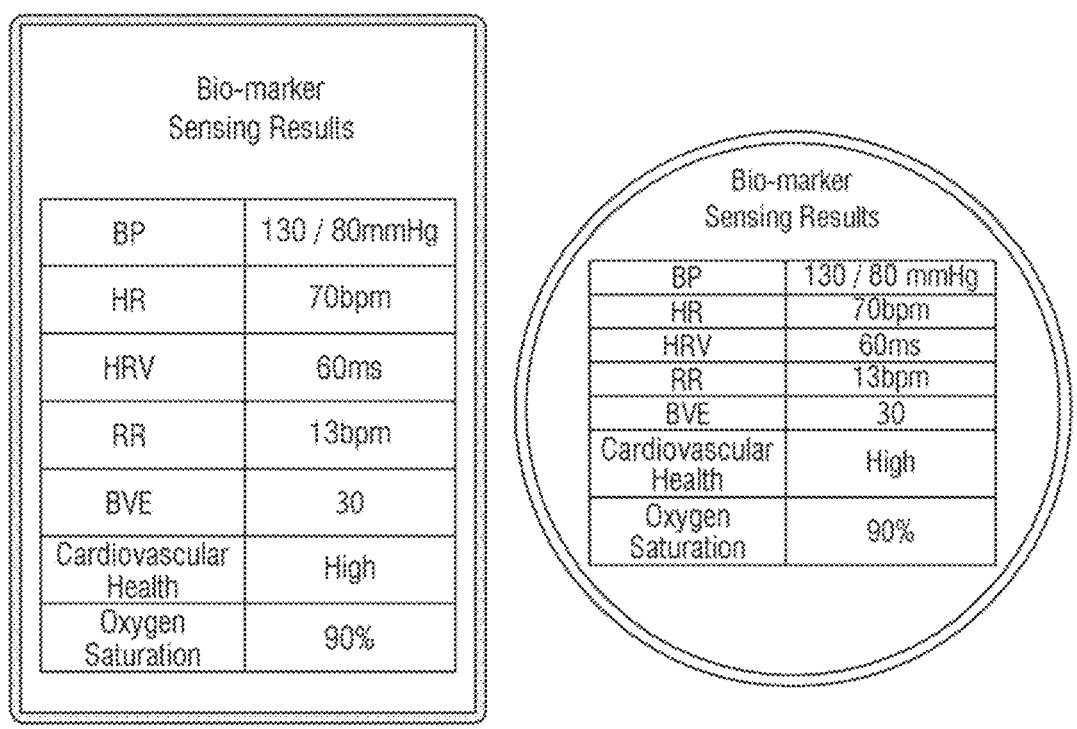
FIG. 23 is a diagram showing biometric information measurement results detected using the most normally detected pulse wave signal among pulse wave signals detected by each display device.

FIG. 23 is a diagram showing biometric information measurement results detected using the most normally detected pulse wave signal among pulse wave signals detected by each display device.

Referring to FIG. 23, the main driving circuit 200 formed at any one display device 10 such as a mobile display device or a watch type display device may measure at least one piece of biometric information by selecting any one pulse wave signal PPG among the first to fourth pulse wave signals received from the main driving circuits 200 of different display devices 10.

The main driving circuit 200 may analyze the selected pulse wave signal to obtain the biometric information such as the blood pressure BP, the heart rate HR, the heart rate variability HRV, the respiratory rate RR, the blood vessel elasticity BVE, the cardiovascular disease (or the cardiovascular health analysis result score), the oxygen saturation, or the like, and may display the obtained result on the application program screen.

Figure 24:
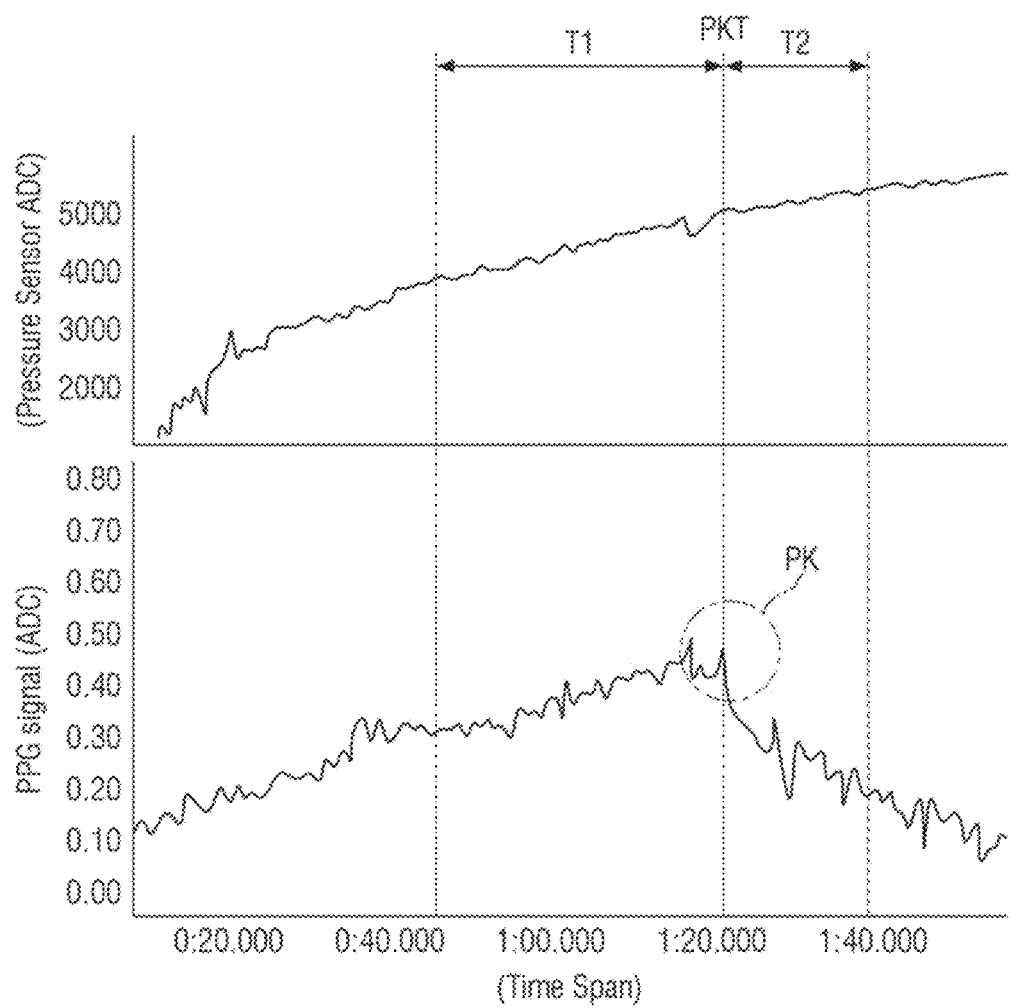
FIG. 24 is a graph illustrating a method for calculating blood pressure information among biometric information according to one embodiment.

FIG. 24 is a graph illustrating a method for calculating blood pressure information among biometric information according to one embodiment.

Referring to FIG. 24, during the systole of the heart, the blood ejected from the left ventricle of the heart moves to the peripheral tissues, and thus the blood volume in the arterial side increases. Further, when the heart contracts, red blood cells carry more oxygen hemoglobin to the peripheral tissues. When the heart relaxes, the heart receives a partial influx of blood from the peripheral tissues. When light is irradiated to peripheral blood vessels, the irradiated light is absorbed by the peripheral tissues. Light absorbance depends on hematocrit and blood volume. The light absorbance may have a maximum value when the heart contracts and may have a minimum value when the heart relaxes. Therefore, light sensed by the light sensing element PD may be the least when the heart contracts and may be the most when the heart relaxes.

Further, when the user puts the finger F on the display panel 100 and lifts it off in the blood pressure measurement mode, a force (e.g., contact force) applied to the force sensing unit PSU may gradually increase to reach a maximum value, and then may gradually decrease. When the contact force increases, blood vessels may be narrowed, resulting in no blood flow. When the contact force decreases, the blood vessels expand, and thus blood flows again. A further decrease of the contact force results in greater blood flow. Therefore, the change in the amount of light sensed by the light sensing pixel LSP may be proportional to the change in blood flow. Accordingly, the main driving circuit 200 generates the pulse wave signals PPG according to the pressure applied by a user based on a pressure data value (e.g., ADC of the pressure sensing unit) that is calculated by the pressure sensing unit PSU and digitally converted and the optical signal (e.g., PPG signal ratio) according to the amount of light sensed by the light sensing element PD. The pulse wave signals PPG may have a waveform vibrating according to the cardiac cycle.

The main driving circuit 200 may estimate blood pressures of the blood vessels of the finger F based on time differences between time points PKT corresponding to peaks PK of the calculated pulse wave signals PPG and time points corresponding to peaks of the filtered pulse wave. For example, the main driving circuit 200 may calculate pulse wave signals during preset periods T1 and T2 before and after the time points PKT corresponding to the peaks PK of the calculated pulse wave signal, and may detect blood pressure according to differences between the pulse wave signals. Among the estimated blood pressure values, a maximum blood pressure value may be determined as a systolic blood pressure value, and a minimum blood pressure value may be determined as a diastolic blood pressure value. Further, additional blood pressure values such as an average blood pressure value or the like may be calculated using the estimated blood pressure values.

Figure 25:
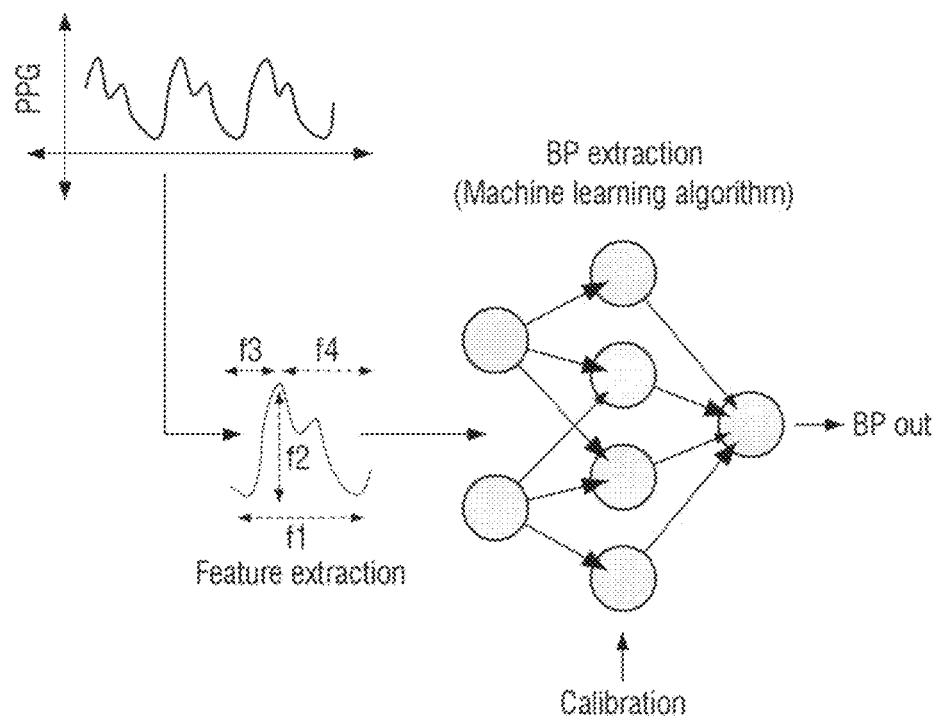
FIG. 25 is a diagram illustrating a blood pressure information calculation method using a machine learning algorithm according to another embodiment of the present disclosure.

FIG. 25 is a diagram illustrating a blood pressure information calculation method using a machine learning algorithm according to another embodiment of the present disclosure.

Referring to FIG. 25, the main driving circuit 200 may learn signal features (for example, signal feature points) of the pulse wave signals PPG using a machine learning algorithm, and may detect the information on the blood pressure BP according to a signal feature change rate of the pulse wave signals PPG.

For example, the main driving circuit 200 sets an initial value or a reference value for each of a pulse width (f1, for example, systolic and diastolic cycles), an amplitude (f2, for example, systolic blood pressure), a pulse width of the systolic cycle (f3, for example, systolic cycle), a diastolic cycle (f4, for example, pulse width of the diastolic cycle) of each of the pulse wave signals PPG. Thereafter, the main driving circuit 200 detects changes in the characteristics of the pulse wave signals PPG inputted in real time, comparing them with the initial value or the reference value of each of the characteristics. For example, main driving circuit 200 detects the magnitudes of changes in the systolic and diastolic cycles, changes in the systolic blood pressure, changes in the systolic cycle, and changes in the diastolic cycle, and storing these as learning data. The main driving circuit 200 may output the information on the blood pressure BP according to the feature change rate or the magnitude of changes of the pulse wave signals PPG compared to the initial value or the reference value of each of the characteristics.

The method for measuring the blood pressure described above is only an example. For example, various other methods are disclosed in Korean Patent Application Publication No. 10-2018-0076050, Korean Patent Application Publication No. 10-2017-0049280, and Korean Patent Application Publication No. 10-2019-0040527, the disclosures of which are incorporated by reference in their entireties.

Figure 26:
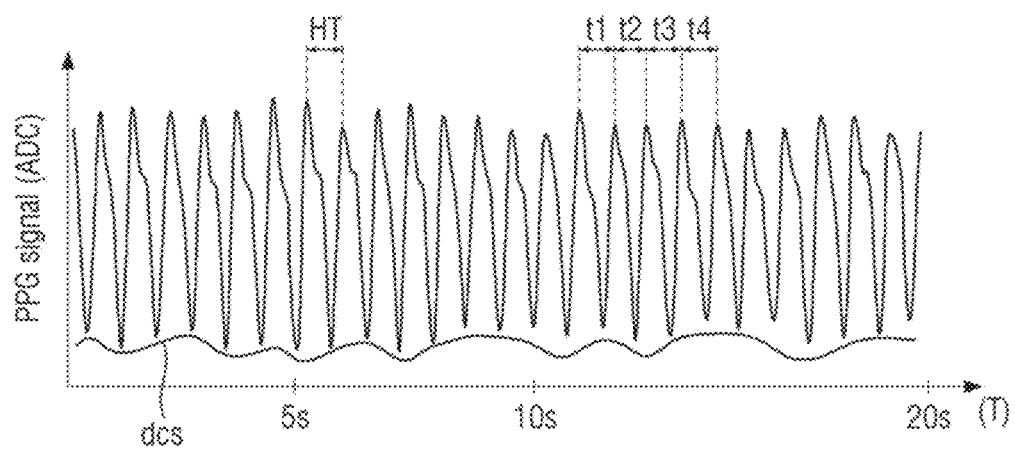
FIG. 26 is a graph illustrating a method for calculating information on heart rate and respiration among biometric information according to one embodiment.

FIG. 26 is a graph illustrating a method for calculating information on heart rate and respiration among biometric information according to one embodiment.

Referring to FIG. 26, the main driving circuit 200 samples pulse wave signals during a preset sampling period before and after the time points PKT corresponding to the peaks PK of the pulse wave signal, and detects a high pulse generation cycle HT of the sampled pulse wave signals PPG. Further, the number of high pulses generated for a preset reference period (for example, 60 seconds) may be counted for the sampled pulse wave signals PPG to detect biometric information on the heart rate cycle and the heart rate HR.

Further, the main driving circuit 200 detects the heart rate cycle, which corresponds to the high pulse generation circuit HT, and the heart rate cycle changes t1, t2, t3 and t4 of high pulses for each preset reference period for the peaks PK of the pulse wave signal to detect the heart rate variability HRV according to the heart rate cycle change rate.

Additionally, the main driving circuit 200 sequentially detects the generation cycle and the magnitude value of low pulses of the sampled pulse wave signals PPG. Then, the change cycle of a magnitude value dcs of low pulses may be detected in units of preset reference periods (for example, 60 seconds) to detect the respiratory change state and the respiratory rate RR of a user. At this time, the cycle in which the magnitude value dcs of low pulses increases and the cycle in which the magnitude value dcs of low pulses decreases may be analyzed to detect the respiratory change state and the respiratory rate RR of the user using the increasing cycle and the decreasing cycle of the magnitude value dcs of low pulses.

Figure 27:
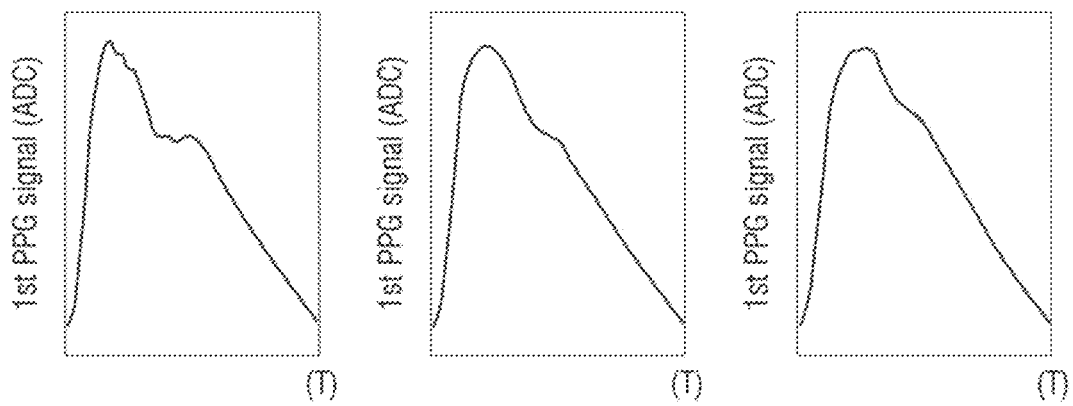
FIG. 27 is a graph illustrating a method for calculating information on blood vessel elasticity among biometric information according to one embodiment.

FIG. 27 is a graph illustrating a method for calculating information on blood vessel elasticity among biometric information according to one embodiment.

Referring to FIG. 27, the main driving circuit 200 may set and obtain the blood vessel elasticity BVE by expanding and analyzing the high pulse variation of the sampled pulse wave signals PPG.

When the blood flow increases due to heartbeat, the pulse wave signal is changed to a high pulse form, and when the blood flow decreases, the pulse wave signal is changed again to a low pulse form. If the blood flow changes rapidly due to the shape of the blood vessel during the period in which the blood flow increases or decreases, the change in the blood flow may be quickly relaxed or slowed depending on the elasticity of the blood vessel. Accordingly, the main driving circuit 200 sets and obtains the blood vessel elasticity BVE using a value corresponding to the magnitude of changes in high pulses by expanding and analyzing the high pulse change form of the pulse wave signals PPG.

Figure 28:
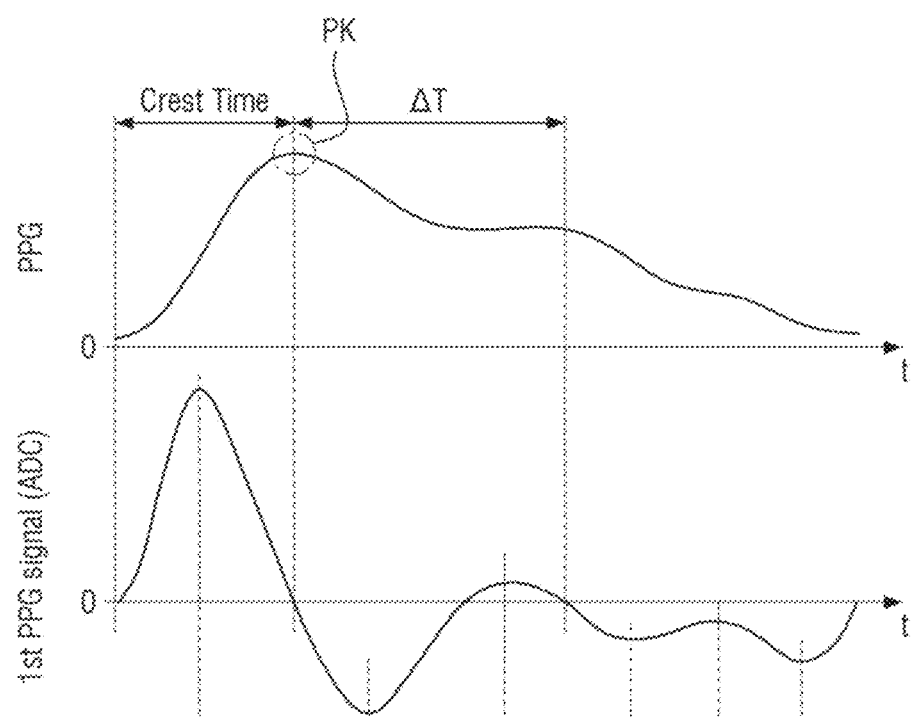
FIG. 28 is a graph illustrating a method for calculating information on cardiovascular disease among biometric information according to one embodiment.

FIG. 28 is a graph illustrating a method for calculating information on cardiovascular disease among biometric information according to one embodiment.

Referring to FIG. 28, the main driving circuit 200 may set and obtain a cardiovascular disease evaluation score (or a cardiovascular health analysis result score) by differentiating and expanding and analyzing the high pulse change form of the sampled pulse wave signals PPG. For example, the main driving circuit 200 detects a period (Crest Time) in which the pulse wave signals PPG reach the peak PK in a high pulse form, and time variation ΔT in which the pulse wave signals PPG fall compared to the period (Crest Time) in which the pulse wave signals PPG reach the peak PK. As the period (Crest Time) in which the pulse wave signals PPG reach the peak PK in a high pulse form increases, the risk of heart disease increases. Accordingly, the main driving circuit 200 may set and obtain the cardiovascular disease evaluation score (or the cardiovascular health analysis result score) in inverse proportion to the period (Crest Time) in which the pulse wave signals PPG reach the peak PK in a high pulse form.

Figure 29:
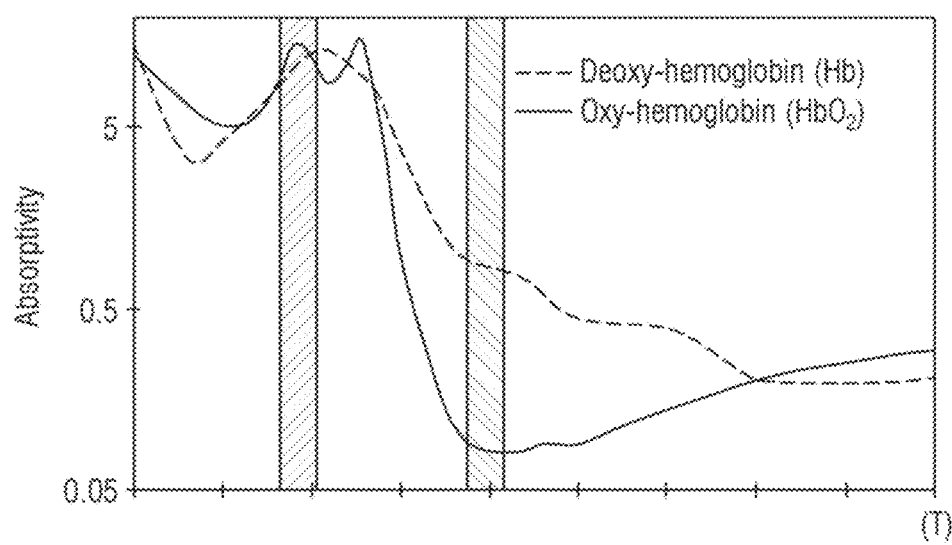
FIG. 29 is a graph illustrating a method for calculating information on oxygen saturation among biometric information according to one embodiment.

FIG. 29 is a graph illustrating a method for calculating information on oxygen saturation among biometric information according to one embodiment.

Referring to FIG. 29, when the heart contracts, red blood cells carry more oxygen hemoglobin to peripheral tissues. On the other hand, when the heart relaxes, the heart receives a partial influx of blood from the peripheral tissues. Using this, the main driving circuit 200 detects a deoxy-hemoglobin (Hb) value using the magnitude change of the pulse wave signals PPG detected by the green light, and detects a $HbO_2$ (Oxy-hemoglobin) value using the magnitude change of the pulse wave signals PPG detected by the red light.

The main driving circuit 200 may detect the oxygen saturation ($SpO_2$) using the following Eq. (2).

$$SpO_2 = HpO_{2/}SpO_2 + Hb \qquad (2)$$

The main driving circuit 200 may display the biometric information such as the blood pressure BP, the heart rate HR, the heart rate variability HRV, the respiratory rate RR, the blood vessel elasticity BVE, the cardiovascular disease (or the cardiovascular health analysis result score), the oxygen saturation ($SpO_2$), or the like on the application program screen.

In concluding the detailed description, those skilled in the art will appreciate that many variations and modifications can be made to the embodiments without substantially departing from the principles of the present disclosure. Therefore, the disclosed embodiments of the disclosure are used in a generic and descriptive sense and not for purposes of limitation.

What is claimed is:

1. A display device comprising:
   display pixels arranged in a display area of a display panel;
   light sensing pixels arranged in the display area;
   a display scan driver configured to drive the display pixels to emit light;
   a light sensing scan driver configured to drive the light sensing pixels to sense light; and
   a main driving circuit configured to measure a user's biometric information using light sensing signals received from the light sensing pixels,
   wherein the main driving circuit displays a preset application program screen during a biometric information measurement period to guide the user's pulse wave signal detection process, and measures the biometric information using pulse wave signals determined to have high accuracy among pulse wave signals detected during the biometric information measurement period,
   wherein the main driving circuit displays a touch sensing area touched by the user's body part on the application program screen in the display area,
   displays waveforms of the pulse wave signals detected in real time on a display window of the application program screen, and
   displays a detection period of the pulse wave signals required to measure the biometric information and a period in which the pulse wave signals are detected,
   wherein the main driving circuit generates the pulse wave signals corresponding to magnitudes of the light sensing signals and changes in the magnitudes of the light sensing signals,
   calculates an average magnitude value of high pulses and an average magnitude value of low pulses in real time by analyzing changes in magnitudes of the high pulses and magnitudes of the low pulses of the pulse wave signals in real time, and
   sets a normal pulse wave signal detection period or an inaccurate pulse wave signal detection period in real time according to a comparison result between the average magnitude value of the high pulses and a preset high threshold and a comparison result between the average magnitude value of the low pulses and a preset low threshold.

2. The display device of claim 1, wherein the main driving circuit sets the inaccurate pulse wave signal detection period when the average magnitude value of the high pulses is smaller than the preset high threshold during a plurality of preset frame periods, or when the average magnitude value of the low pulses is smaller than the preset low threshold during the plurality of preset frame periods.

3. The display device of claim 2, wherein the main driving circuit generates an image or a capacitance profile based on signal values of the light sensing signals, detects a touch area of the user's body part based on the image or the capacitance profile, sets the inaccurate pulse wave signal detection period when the detected touch area is smaller than a reference area,
- displays a touch guide message on the application program screen so that the user's body part can be accurately touched and a touch state can be maintained during the inaccurate pulse wave signal detection period, and
- displays the waveforms of the pulse wave signals displayed in real time on the display window and the touch guide message that changes to a first color.

4. The display device of claim 3, wherein the main driving circuit displays a touch guide message on the application program screen so that a normal touch state can be maintained when the normal pulse wave signal detection period is set, and
- displays the waveforms of the pulse wave signals displayed in real time on the display window and the touch guide message that changes to a second color.

5. The display device of claim 4, wherein the main driving circuit analyzes each of a high pulse cycle and a high pulse cycle change of the pulse wave signals detected during the normal pulse wave signal detection period, a high pulse magnitude and a change of the high pulse magnitude, a low pulse magnitude and a change of the low pulse magnitude, a waveform change of the high pulse, a period in which the high pulse reaches a peak, and a difference in pulse magnitude between the pulse wave signals respectively detected by green light and red light,
- obtains at least one piece of biometric information among blood pressure, heart rate, heart rate variability, respiratory rate, blood vessel elasticity, a cardiovascular disease analysis result, and oxygen saturation according to each analysis result, and displays the obtained biometric information on the application program screen.

6. A display device comprising:
- display pixels arranged in a display area of a display panel;
- light sensing pixels arranged in the display area;
- a display scan driver configured to drive the display pixels to emit light;
- a light sensing scan driver configured to drive the light sensing pixels to sense light; and
- a main driving circuit configured to measure a user's biometric information using light sensing signals received from the light sensing pixels,
- wherein the main driving circuit displays a preset application program screen during a biometric information measurement period to guide the user's pulse wave signal detection process, and measures the biometric information using pulse wave signals determined to have high accuracy among pulse wave signals detected during the biometric information measurement period,
- wherein the main driving circuit displays a touch sensing area touched by the user's body part on the application program screen in the display area,
- displays waveforms of the pulse wave signals detected in real time on a display window of the application program screen, and
- displays a detection period of the pulse wave signals required to measure the biometric information and a period in which the pulse wave signals are detected,
- wherein the main driving circuit generates first pulse wave signals corresponding to magnitudes of the light sensing signals and changes in the magnitudes of the light sensing signals,
- receives at least one second pulse wave signal or an $n^{th}$ pulse wave signal from a main driving circuit formed in at least one other adjacent display device,
- compares and analyzes the first and second pulse wave signals or at least two pulse wave signals among the first to $n^{th}$ pulse wave signals, and measures the biometric information by selecting and using any one pulse wave signal according to the analysis result.

7. The display device of claim 6, wherein the main driving circuit calculates and compares an average magnitude value of high pulses and an average magnitude value of low pulses of the first and second pulse wave signals or the first to $n^{th}$ pulse wave signals, selects any one of the pulse wave signals according to the comparison result, and measures the biometric information by analyzing the selected pulse wave signal.

8. The display device of claim 7, wherein the main driving circuit compares average magnitude values of high pulses of the first and second pulse wave signals or the first to $n^{th}$ pulse wave signals with each other, and selects any one pulse wave signal having the largest average magnitude value of the high pulses to measure the biometric information,
- measures the biometric information by selecting any one pulse wave signal having a median value among the average magnitude values of the high pulses compared with each other,
- compares average magnitude values of low pulses of the first and second pulse wave signals or the first to $n^{th}$ pulse wave signals with each other, and selects any one pulse wave signal having the smallest average magnitude value of the low pulses to measure the biometric information, or
- measures the biometric information by selecting any one pulse wave signal having a median value among the average magnitude values of the low pulses compared with each other.

9. The display device of claim 6, wherein the main driving circuit calculates an average magnitude value of high pulses and an average magnitude value of low pulses of the first and second pulse wave signals or the first to $n^{th}$ pulse wave signals,
- compares the calculated average magnitude value of the high pulses with a preset high threshold, compares the average magnitude value of the low pulses with a preset low threshold, selects any one of the pulse wave signals according to the comparison result, and measures the biometric information by analyzing the selected pulse wave signal.

10. The display device of claim 9, wherein the main driving circuit selects any one pulse wave signal having the largest average magnitude value of high pulses compared to the preset high threshold to measure the biometric information, or
- selects any one pulse wave signal having the largest average magnitude value of low pulses compared to the preset low threshold to measure the biometric information.

* * * * *